US011795429B2

(12) United States Patent
Bitterfield et al.

(10) Patent No.: US 11,795,429 B2
(45) Date of Patent: *Oct. 24, 2023

(54) COMPOSITIONS COMPRISING SOLID PARTICLES

(71) Applicant: Lindy Biosciences, Inc., Research Triangle Park, NC (US)

(72) Inventors: Deborah Lee Bitterfield, Raleigh, NC (US); Michael Quinn Doherty, Hillsborough, NC (US)

(73) Assignee: Lindy Biosciences, Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/058,306

(22) Filed: Nov. 23, 2022

(65) Prior Publication Data

US 2023/0093954 A1 Mar. 30, 2023

Related U.S. Application Data

(63) Continuation of application No. 17/428,063, filed as application No. PCT/US2020/016743 on Feb. 5, 2020.

(60) Provisional application No. 62/801,225, filed on Feb. 5, 2019.

(51) Int. Cl.

| | |
|---|---|
| ***C12N 1/02*** | (2006.01) |
| ***C07K 1/14*** | (2006.01) |
| ***C07K 1/30*** | (2006.01) |
| ***C07K 1/00*** | (2006.01) |
| ***A61K 49/00*** | (2006.01) |
| ***A61K 49/04*** | (2006.01) |

(52) U.S. Cl.
CPC .................................... *C12N 1/02* (2013.01)

(58) Field of Classification Search
None
See application file for complete search history.

(56) References Cited

U.S. PATENT DOCUMENTS

| | | | |
|---|---|---|---|
| 6,264,990 | B1 | 7/2001 | Knepp et al. |
| 8,013,022 | B2 | 9/2011 | Deangelo et al. |
| 8,110,209 | B2 | 2/2012 | Prestrelski et al. |
| 8,299,025 | B2 | 10/2012 | Alessi et al. |
| 8,333,995 | B2 | 12/2012 | Brown et al. |
| 8,512,754 | B2 | 8/2013 | Needham |
| 8,597,918 | B2 | 12/2013 | Clark et al. |
| 8,673,264 | B2 | 3/2014 | Baylatry et al. |
| 8,709,827 | B2 | 4/2014 | Slager et al. |
| 8,728,525 | B2 | 5/2014 | Brown et al. |
| 8,779,094 | B2 | 7/2014 | Johnston et al. |
| 8,802,095 | B2 | 8/2014 | Houston et al. |
| 8,895,033 | B2 | 11/2014 | Houchin et al. |
| 8,932,715 | B2 | 1/2015 | Moore et al. |
| 9,072,668 | B2 | 7/2015 | Dai et al. |
| 9,643,996 | B2 | 5/2017 | Petrel et al. |
| 9,725,694 | B2 | 8/2017 | Edinger et al. |
| 11,077,059 | B2 | 8/2021 | Coffman et al. |
| 11,459,376 | B2 | 10/2022 | Brown et al. |
| 2006/0120992 | A1 | 6/2006 | Moore et al. |
| 2007/0207210 | A1 | 9/2007 | Brown et al. |
| 2008/0248122 | A1 | 10/2008 | Rashba-Step et al. |
| 2009/0234146 | A1 | 9/2009 | Cooney et al. |
| 2010/0009007 | A1 | 1/2010 | Darvari et al. |
| 2011/0223208 | A1 | 9/2011 | Hill et al. |
| 2012/0024797 | A1 | 2/2012 | Kale |
| 2012/0046225 | A1 | 2/2012 | Prestrelski et al. |
| 2012/0232001 | A1 | 9/2012 | Prestrelski et al. |
| 2013/0309226 | A1 | 11/2013 | Armstrong et al. |
| 2014/0161797 | A1 | 6/2014 | Chen et al. |
| 2015/0025260 | A1 | 1/2015 | Bijl et al. |
| 2017/0119854 | A1 | 5/2017 | Alessi et al. |
| 2020/0253875 | A1 | 8/2020 | Coffman et al. |
| 2021/0220289 | A1 | 7/2021 | Coffman et al. |
| 2021/0309724 | A1* | 10/2021 | Brown .................. A61K 47/14 |

(Continued)

FOREIGN PATENT DOCUMENTS

| | | |
|---|---|---|
| CN | 102985528 A | 3/2013 |
| CN | 103393601 A | 11/2013 |

(Continued)

OTHER PUBLICATIONS

Aniket et al. "Enzyme Dehydration Using Microglassification™ Preserves the Protein's Structure and Function" Journal of Pharmaceutical Sciences, 104:640-651 (2015).
Aniket et al. "Microglassification™: A Novel Technique for Protein Dehydration" Journal of Pharmaceutical Sciences, 103:810-820 (2014).
Bitterfield et al. "An Activity-Based Dissolution Model for Solute-Containing Microdroplets" Langmuir, 32 (48):12749-12759 (2016).
Bitterfield et al. "An alternative dehydration process enabling high concentration delivery of biologics" poster, 1 page (2016).

(Continued)

*Primary Examiner* — Daniel E Kolker
*Assistant Examiner* — James L Rogers
(74) *Attorney, Agent, or Firm* — Myers Bigel, P.A.

(57) ABSTRACT

Described herein are isolated cell culture components such as, e.g., biologics and/or lipids, and methods for isolating cell culture components from a liquid cell culture medium. Methods of the present invention may include contacting a dehydration composition and a liquid cell culture medium comprising a target component to form a mixture; forming an at least partially dehydrated component in the mixture; and separating the at least partially dehydrated component from the mixture, thereby providing an isolated component. In some embodiments, the isolated component comprises the at least partially dehydrated component. In some embodiments, the isolated component is present in a composition (e.g., liquid phase) separated from the at least partially dehydrated component.

30 Claims, 15 Drawing Sheets

(56) References Cited

U.S. PATENT DOCUMENTS

| | | | |
|---|---|---|---|
| 2021/0322317 | A1 | 10/2021 | Coffman et al. |
| 2022/0119760 | A1 | 4/2022 | Bitterfield et al. |

FOREIGN PATENT DOCUMENTS

| | | | | |
|---|---|---|---|---|
| EP | 2157967 B1 | | 1/2013 | |
| EP | 3459529 A1 | | 3/2019 | |
| WO | 9954355 A1 | | 10/1999 | |
| WO | 03035031 A1 | | 5/2003 | |
| WO | 2005112893 A1 | | 12/2005 | |
| WO | 2011127167 A1 | | 10/2011 | |
| WO | 2012121754 A1 | | 9/2012 | |
| WO | 2013067022 A1 | | 5/2013 | |
| WO | WO-2016016665 A1 | * | 2/2016 | ........... A61K 31/495 |
| WO | 2019023392 A1 | | 1/2019 | |
| WO | 2021212019 A1 | | 10/2021 | |

OTHER PUBLICATIONS

Bitterfield et al. "Microglassification ™: Enabling Solid Suspensions for High-Concentration Protein Formulations" poster, 1 page (2015).

Bitterfield et al. "Microglassification™: Novel & Rapid Protein Dehydration" poster, 1 page (2018).

Bitterfield et al. "Microglassification™: Rapid protein dehydration enabling high concentration suspension formulations" poster, 1 page (2016).

Bitterfield et al. "Utilization of a Rapid Dehydration Technology for the Production of High-Concentration Suspension Formulations" poster, 1 page (2018).

Bitterfield, Deborah "A Rapid Dehydration Process for the Stability and Delivery of Biologics" Presentation from the Bioprocessing Summit, Boston, MA (24 pages) (Aug. 14, 2019).

Bitterfield, Deborah "Delivery of High-Concentration Protein Suspensions" Presentation from the Bioprocessing Summit, Boston, MA (21 pages) (Aug. 15, 2018).

Bitterfield, Deborah "Microglassification™ for High-Concentration Protein Suspensions" Presentation from the 7th Annual Partnership Opportunities in Drug Delivery (PODD), Boston, MA (7 pages) (Oct. 20, 2017).

Bitterfield, Deborah "Particle Engineering Platform for High-Concentration Protein Suspensions" Presentation from the Bioprocessing Summit, Boston, MA (13 pages) (Aug. 23, 2017).

Bowen et al. "Investigating High-Concentration Monoclonal Antibody Powder Suspension in Nonaqueous Suspension Vehicles for Subcutaneous Injection" Journal of Pharmaceutical Sciences, 101(12):4433-4443 (2012).

Dadon, Daniel B. "Revolutionizing the Delivery of Biologics" Presentation (26 pages) (2017).

Dai, Weiguo "Viscosity/Injectability of Monoclonal Antibody Powder Suspension Formulations" Presentation from the AAPS Annual Meeting (27 pages) (Nov. 4, 2014).

Doherty et al. "Examination of Processing Parameters of Microglassification™, a Novel & Rapid Dehydration Technology" poster, 1 page (2018).

Doherty et al. "Microglassification ™: A Novel Dehydration Process Enabling Low Viscosity, Highly Concentrated Injectable Suspensions of Biologics" poster, 1 page (2018).

Doherty et al. "Process Optimization of a Novel Dehydration Technology for Low-Viscosity High-Concentration Protein Formulations" poster, 1 page (2017).

Duncan et al. "Test of the Epstein-Plesset Model for Gas Microparticle Dissolution in Aqueous Media: Effect of Surface Tension and Gas Undersaturation in Solution" Langmuir, 20(7):2567-2578 (2004).

Extended European Search Report corresponding to European Patent Application No. 20751976.0 (11 pages) (dated Oct. 5, 2022).

Herrmann et al. "Biodegradable, somatostatin acetate containing microspheres prepared by various aqueous and non-aqueous solvent evaporation methods" European Journal of Pharmaceutics and Biopharmaceutics, 45(1):75-82 (1998).

International Search Report and the Written Opinion of the International Searching Authority corresponding to International Patent Application No. PCT/US2020/016743 (13 pages) (dated Apr. 29, 2020).

Lindy Biosciences "Microglassification™ (MG): Protein Dehydration Platform" poster, 1 page (2018).

Miller et al. "Low Viscosity Highly Concentrated Injectable Nonaqueous Suspensions of Lysozyme Microparticles" Langmuir, 26(2):1067-1074 (2010).

Rickard et al. "Hydration Potential of Lysozyme: Protein Dehydration Using a Single Microparticle Technique" Biophysical Journal, 98(6):1075-1084 (2010).

Rickard, Deborah Lee "Multiphase, Multicomponent Systems: Divalent Ionic Surfactant Phases and Single-Particle Engineering of Protein & Polymer Glasses" PhD Thesis, Dept. of Mechanical Engineering & Materials Science, Duke University (320 pages) (2011).

Ryle et al. "Microglassification: A Novel & Rapid Dehydration Technology" poster, 1 page (2020).

Savage et al. "Microglassification™ to Enable Delivery of Highly Concentrated Protein Particle Suspensions" poster, 1 page (2020).

Shekunov et al. "Particle Size Analysis in Pharmaceutics: Principles, Methods and Applications" Pharmaceutical Research, 24:203-227 (2007).

Srinivasan et al. "Non-aqueous suspensions of antibodies are much less viscous than equally concentrated aqueous solutions" Pharmaceutical Research, 30:1749-1757 (2013).

Su et al. "The effect of hydrogen bonding on the diffusion of water in n-alkanes and n-alcohols measured with a novel single microdroplet method" The Journal of Chemical Physics, 132(4):044506 (2010).

U.S. Appl. No. 62/899,907, filed Sep. 13, 2019 (156 pages).

U.S. Appl. No. 62/899,981,; filed Sep. 13, 2019 (135 pages).

U.S. Appl. No. 63/024,703, filed May 14, 2020 (176 pages).

Vehring, Reinhard "Pharmaceutical Particle Engineering via Spray Drying" Pharmaceutical Research, 25 (5):999-1022 (2008).

Wang et al. "Nanocarriers and Their Loading Strategies" Advanced Healthcare Materials, 8(6):e1801002 (2019).

* cited by examiner

COMPOSITIONS COMPRISING SOLID PARTICLES

RELATED APPLICATION INFORMATION

This application is a continuation application of U.S. patent application Ser. No. 17/428,063, filed Aug. 3, 2021, which is a 35 U.S.C. § 371 national phase application of International Application No. PCT/US2020/016743, filed Feb. 5, 2020, which claims the benefit of and priority to U.S. Provisional Patent Application Ser. No. 62/801,225, filed Feb. 5, 2019, the disclosure of each of which is incorporated herein by reference in their entirety.

FIELD

The present invention relates to isolated cell culture components such as, e.g., biologics and/or lipids, and to methods for isolating cell culture components from a liquid cell culture medium.

BACKGROUND

Pharmaceutical companies and manufacturers are seeing a significant change in their drug development and manufacturing processes due to the significant growth and transition into more complex biological-based therapeutics. This industry-wide growth in biologics is a major driving force in the production of millions of units of bulk biological drug substances (DS). The transportation of temperature-controlled pharmaceuticals is one of the fastest growing verticals in the global healthcare logistics industry as well. Moreover, biomanufacturing is a key component of biologics production and encompasses a significant share of the biologics market.

Many companies are decoupling bulk drug substance production from the final drug product manufacturing operations. This means that valuable DS must be stored and shipped globally per demand with clinical trials supply and final drug production.

It is well known that freezing can extend the shelf life of biologics. This practice has become a common choice for preserving bulk drug substance. However, the freezing process itself, as well as subsequent thawing, can have detrimental effects on the structure and stability of biomolecules. As freezing occurs, the protein is exposed to a variety of factors that can increase aggregation. Ice crystals create a large surface area where proteins are prone to unfolding. The removal of water into the ice phase results in "cryoconcentration," i.e., solutes (buffer salts, excipients, and the protein itself) become more concentrated and cause pH shifts and local concentration fluctuations. Freezing and thawing rates are largely dependent on volume and vessel size, so they can be inherently difficult to scale in a controlled fashion. Typical jacketed metal freeze-thaw vessels will hold up to 300 L of DS, and take 18 hours to freeze. Further, storage at −20° C. is often not far enough below the glass transition temperature to confer stability. As storage and shipping temperatures decrease, costs increase dramatically.

Challenges continue to arise in biologic manufacturing, as more stringent regulations on manufacturing processes are implemented. Manufacturers are seeing a much greater emphasis on stability and temperature requirements. When companies are required to discard or destroy units of a biologic drug substance, the result is considerably higher losses in investment and extended delays in the product development timeline. Loss is present across the industry in high numbers: over $15 billion in product losses occur every year in the pharmaceutical industry due to temperature excursions alone; 25% of vaccines reach their destination degraded because of incorrect shipping; 30% of scrapped pharmaceuticals can be attributed to logistics issues; and 20% of temperature-sensitive products are damaged during transport due to a broken cold chain.

Lyophilization can be used to confer stability to final drug product forms. However, it typically requires too much up-front development (e.g., identifying proper cycle conditions) to be useful at this stage, and it suffers from the freezing stresses mentioned above. In addition, it is only a batch process, is a lengthy process (a single batch can take several days), and capital equipment and energy costs are extensive.

Spray drying has been investigated as a potential alternative processing technique for biologics. However, it is frequently plagued by reduced product yield and aggregation issues. Many proteins are surface active and will aggregate at the high-energy air-water interface. Required outlet temperatures can also be a problem for temperature-sensitive proteins. Large excipient loads (e.g., from about 50%-90% w/w) are often required to stabilize proteins, and these excipients have been shown to segregate from the protein within the particle, possibly reducing their effectiveness.

SUMMARY

A first aspect of the present invention is directed to a method of isolating a component (e.g., a biologic or lipid) from a liquid cell culture medium, the method comprising: contacting a dehydration composition (e.g., a first organic solvent) and a liquid cell culture medium comprising the component to form a mixture; forming an at least partially dehydrated component in the mixture; and separating the at least partially dehydrated component from the mixture, thereby providing an isolated component. In some embodiments, the isolated component comprises the at least partially dehydrated component. In some embodiments, the isolated component is present in a composition (e.g., a liquid phase) separated from the at least partially dehydrated component.

Another aspect of the present invention is directed to a composition comprising a plurality of solid amorphous particles (e.g., microparticles). In some embodiments, at least a portion of the plurality of solid amorphous particles are solid amorphous particles comprising a biologic (e.g., a protein, peptide, polynucleotide, etc.).

A further aspect of the present invention is directed to an isolated biologic, wherein the isolated biologic is at least partially dehydrated.

Another aspect of the present invention is directed to an isolated hydrophobic component (e.g., a lipid and/or steroid). The isolated hydrophobic component may be at least partially separated from at least partially dehydrated components and/or water soluble components present in a liquid cell culture medium.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

DETAILED DESCRIPTION OF EXAMPLE EMBODIMENTS

Figure 1:
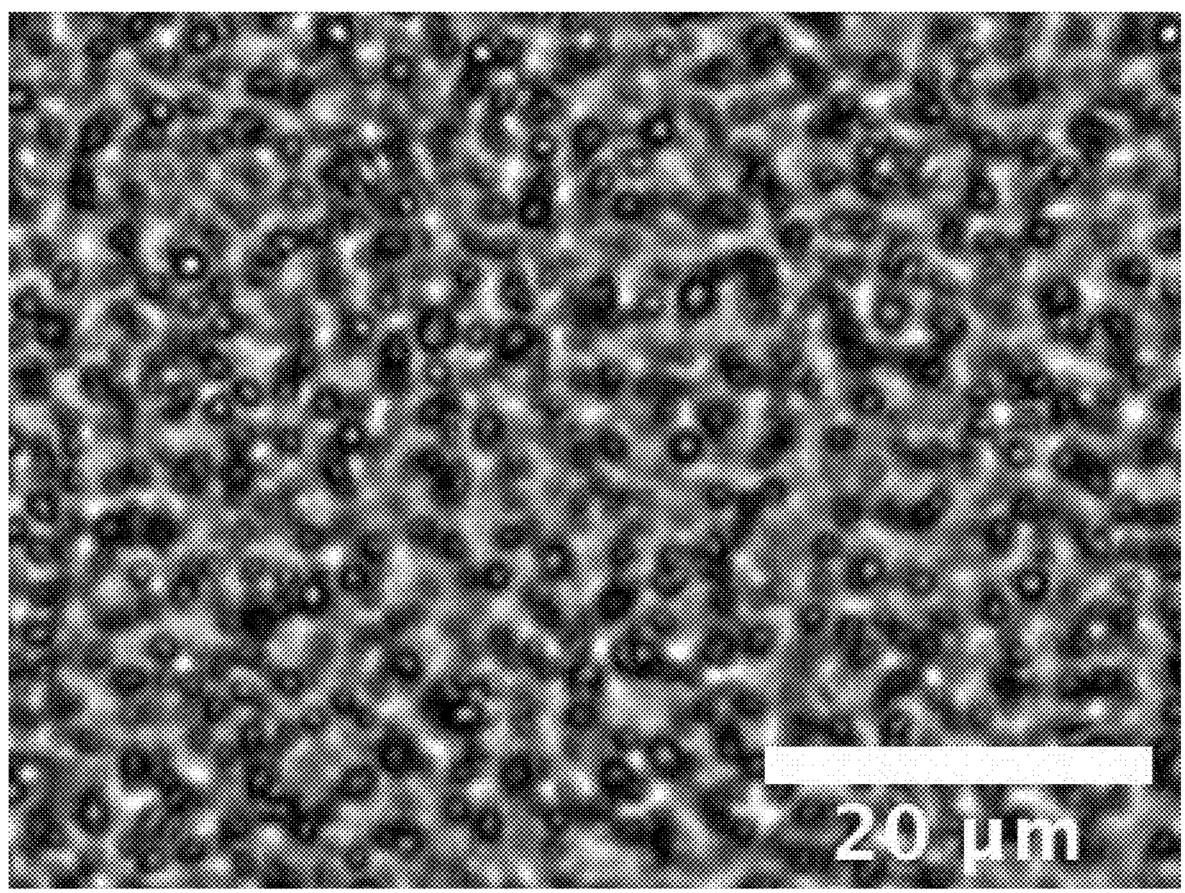
FIG. 1 is an image of a suspension including microglassified lysozyme particles.

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used in the description of the invention herein is for the purpose of describing particular embodiments only and is not intended to be limiting of the invention. As used in the description of the invention and the appended claims, the singular forms “a,” “an” and “the” are intended to include the plural forms as well, unless the context clearly indicates otherwise.

It will be understood that, although the terms “first,” “second,” etc. may be used herein to describe various elements, these elements should not be limited by these terms. These terms are only used to distinguish one element from another. Thus, a “first” element discussed below could also be termed a “second” element without departing from the teachings of the present invention. The sequence of operations (or steps) is not limited to the order presented in the claims or figures unless specifically indicated otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. All publications, patent applications, patents and other references mentioned herein are incorporated by reference in their entirety. In case of a conflict in terminology, the present specification is controlling.

Also as used herein, “and/or” refers to and encompasses any and all possible combinations of one or more of the associated listed items, as well as the lack of combinations when interpreted in the alternative (“or”).

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase “consisting essentially of” (and grammatical variants) is to be interpreted as encompassing the recited materials or steps “and those that do not materially affect the basic and novel characteristic(s)” of the claimed invention. See, In re Herz, 537 F.2d 549, 551-52, 190 U.S.P.Q. 461, 463 (CCPA 1976) (emphasis in the original); see also MPEP § 2111.03. Thus, the term “consisting essentially of” as used herein should not be interpreted as equivalent to “comprising.”

It will also be understood that, as used herein, the terms “example,” “exemplary,” and grammatical variations thereof are intended to refer to non-limiting examples and/or variant embodiments discussed herein, and are not intended to indicate preference for one or more embodiments discussed herein compared to one or more other embodiments.

The term “about,” as used herein when referring to a measurable value such as an amount or concentration and the like, is meant to encompass variations of ±10%, ±5%, ±1%, ±0.5%, or even ±0.1% of the specified value as well as the specified value. For example, “about X” where X is the measurable value, is meant to include X as well as variations of ±10%, ±5%, ±1%, ±0.5%, or even ±0.1% of X. A range provided herein for a measureable value may include any other range and/or individual value therein.

As used herein, the terms "increase," "increases," "increased," "increasing," "improve," "enhance," and similar terms indicate an elevation in the specified parameter of at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more.

As used herein, the terms "reduce," "reduces," "reduced," "reduction," "inhibit," and similar terms refer to a decrease in the specified parameter of at least about 5%, 10%, 15%, 20%, 25%, 30%, 35%, 40%, 45%, 50%, 55%, 60%, 65%, 70%, 75%, 80%, 85%, 90%, 95%, 97%, or 100%.

Provided according to embodiments of the present invention are methods of isolating a component (e.g., a biologic or lipid) from a liquid cell culture medium. The component may be any compound, molecule, and/or biologic present in the liquid cell culture medium. Exemplary liquid cell culture media include, but are not limited to, fermentation broths and/or microbiological cultures. As understood in the art, liquid cell culture media may comprise cells, cell components (e.g., lipids, cell membranes, proteins, DNA, etc.), synthetic materials (e.g., additives for stabilization of the media (e.g., poloxamers such as Poloxamer 188 PRO)), buffers, sugars, and/or the like. For example, a fermentation broth may comprise tryptic soy broth, bacto yeast extract, ammonium chloride, disodium phosphate, potassium phosphate, and/or glucose. Any type of cell may be present in a liquid cell culture medium of the present invention such as, but not limited to, bacterial cells, yeast cells, and/or mammalian cells (e.g., human cells). In some embodiments, a liquid cell culture medium comprises a cell that intracellularly and/or extracellularly expresses a biologic that may be isolated in accordance with a method of the present invention.

A method of the present invention may use a liquid cell culture medium without any modifications (e.g., without adding or removing anything) to the medium compared to prior to the method. For example, the medium may be used directly from cell culture. In some embodiments, a method of the present invention may comprise processing the liquid cell culture medium such as, but not limited to, concentrating, centrifuging, washing, dialyzing, and/or filtering the liquid cell culture medium. One or more processing steps may be used to concentrate the cells and/or remove substances (e.g., salts and/or cells) present in the liquid cell culture medium. The component to be isolated may determine whether cells are to be concentrated or removed. For example, when the component is expressed inside cells, the cells may be concentrated, whereas when the component is extracellularly expressed, the cells may be removed. In some embodiments, a method of the present invention may use a liquid cell culture medium that is diluted such as, e.g., with water or an aqueous solution (e.g., a buffer). In some embodiments, a method of the present invention may use a liquid cell culture medium that is concentrated such as, e.g., via centrifugation and/or filtration.

In some embodiments, a liquid cell culture medium may comprise one or more (e.g., 1, 2, 3, 4, 5, or more) additives. Exemplary additives include, but are not limited to, stabilizers, surfactants, tonicity agents, sugars, salts, antimicrobial agents, antioxidants, reducing agents, etc. In some embodiments, an additive is present in a liquid cell culture medium at a concentration of about 0.01%, 0.1%, or 0.5% to about 1%, 2%, 3%, 4%, 5%, 6%, 7%, 8%, 9%, or 10% by weight of the liquid cell culture medium.

Exemplary surfactants include, but are not limited to, polysorbates (e.g., polysorbate 20 or 80), spans, pegylated fatty esters and ethers (e.g., Laureth-4), sucrose esters, block copolymers (e.g., poloxamers), and/or ethoxylated triglycerides (e.g., ethoxylated castor oil).

Exemplary antimicrobial agents include, but are not limited to, benzoic acid and/or benzyl alcohol. Exemplary antioxidants include, but are not limited to, butylated hydroxy anisole, butylated hydroxy toluene, propyl gallate, tert-butyl hydroquinone, and/or Vitamin E. Exemplary reducing agents include, but are not limited to, glutathione and/or dithiothreitol (DTT).

In some embodiments, an emulsification solvent may be added to a liquid cell culture medium. An emulsification solvent may form an interface with a liquid cell culture medium and/or aqueous composition. Exemplary emulsification solvents include, but are not limited to, alkanes such as, e.g., an alkane having 1-20 carbon atoms (i.e., a C1-C20 alkane) or a C4-C20 alkane (e.g., propane, pentane, hexane, etc.); alcohols (e.g., a C5-C14 alcohol); acetates; esters; ethers; carboxylic acids; (poly)heteroatomic cyclic, acyclic, linear or branched molecules; and/or lactates such as butyl lactate and/or ethyl lactate. In some embodiments, the solvent may include a carbon, nitrogen, and/or sulfur atom. In some embodiments, an emulsification solvent is miscible with a solvent present in a dehydration composition of the present invention. In some embodiments, the emulsification solvent may be an alcohol such as pentanol and/or a lactate such as butyl lactate and/or ethyl lactate.

An emulsification solvent may be present in a liquid cell culture medium in an amount sufficient to form an emulsion (e.g., a water-in-oil emulsion). In some embodiments, an emulsification solvent is present in a liquid cell culture medium in an amount of about 20% or more such as, e.g., about 25%, 30%, 35%, 40%, 45%, 50%, 55%, 60%, 65%, 70%, 75%, 80%, 85%, 90%, 95% or more. In some embodiments, the addition of an emulsification solvent to a liquid cell culture medium may at least partially lyse cells, cell membranes, and/or lipid formations present in the liquid cell culture medium. In some embodiments, an emulsification solvent does not dehydrate a component (e.g., biologic) present in the liquid cell culture medium and/or is not present in the medium in a concentration sufficient to dehydrate the component. In some embodiments, an emulsification solvent removes water from a component (e.g., biologic) present in the liquid cell culture medium in an amount of less than about 10%, 5%, 2%, 1%, 0.5%, or 0.1%. In some embodiments, an emulsification solvent aids in providing a desired particle size for an emulsion comprising the liquid cell culture medium and/or an at least partially dehydrated component.

In some embodiments, an emulsification solvent and water may be added to a liquid cell culture medium separately (e.g., one at a time or concurrently) and/or an emulsification solvent and water may be present in the same composition that is added to a liquid cell culture medium. Water may be present in a composition with an emulsification solvent and/or added with an emulsification solvent to a liquid cell culture medium in an amount that is below or at its solubility limit in the emulsification solvent.

A component separated (e.g., isolated) from a liquid cell culture medium may be hydrophilic (e.g., a biologic) or hydrophobic (e.g., a lipid or steroid). In some embodiments, a method of the present invention isolates a biologic present in a liquid cell culture medium. The biologic may be present in a cell in the liquid cell culture medium and/or present outside a cell in the liquid cell culture medium. In some embodiments, the biologic is intracellularly expressed and/or extracellularly expressed. A "biologic" as used herein refers to an amino acid, peptide, protein, enzyme or fragment thereof, antibody or fragment thereof (e.g., heavy chain, light chain, fusion protein, Fv, and/or Fc), etc.), and/or polynucleotide such as, e.g., an oligonucleotide, DNA, and/or RNA. The biologic may comprise compounds and/or molecules, such as, e.g., those that may be bound to the biologic, such as, e.g., sugars and/or salts. In some embodiments, a biologic may be a biological drug substances (DS) and/or used as a therapeutic agent.

An "isolated component" such as, e.g., an "isolated biologic" or "isolated lipid", as used herein, refer to a component that has been at least partially separated or removed from other components present in the liquid cell culture medium in which the component was present. Thus, an "isolated component" may not be in purified form (e.g., having a purity of greater than 90% by weight of the composition in which it is present). In some embodiments, an "isolated component" (e.g., an isolated biologic) is not in pure form and/or does not have a purity and/or concentration of greater than about 20%, 25%, 30%, 35%, 40%, 45%, 50%, 55%, 60%, 65%, 70%, 75%, 80%, 85%, or 90% by weight of the composition in which it is present. "Isolating" and grammatical versions thereof as used herein refer to at least partially separating or removing one component from other components such as, e.g., separating a plurality of components present in a liquid cell culture medium into at least two groups or phases. In some embodiments, a method of the present invention comprises isolating a water soluble component (e.g., a biologic) and/or a water insoluble component (e.g., a lipid) from a liquid cell culture medium.

In some embodiments, a method of the present invention comprises contacting dehydration composition (e.g., an organic solvent) and a liquid cell culture medium comprising a component (e.g., a biologic or lipid) to form a mixture; forming an at least partially dehydrated component in the mixture; and separating the at least partially dehydrated component from the mixture, thereby providing an isolated component. An "at least partially dehydrated component" as used herein refers to component that has a water activity of less than 1. In some embodiments, the isolated component comprises the at least partially dehydrated component (e.g., an at least partially dehydrated biologic). In some embodiments, the isolated component (e.g., a water insoluble component such as, e.g., a lipid) is present in a composition separated from the at least partially dehydrated component. While an isolated component may be at least partially separated from other components present in the cell culture medium, additional components may be present with the isolated component such as, e.g., host cell proteins, sugars, salts, buffers, and/or additives. The additional components present with an isolated component may also be referred to herein as impurities, and the impurities may be at least partially dehydrated.

A method of the present invention may comprise separating a solid phase from a liquid phase. In some embodiments, the isolated component is present in the solid phase. In some embodiments, the isolated component is present in the liquid phase. Impurities present in a solid phase and/or liquid phase may comprise water soluble components and/or water insoluble components. In some embodiments, impurities present in a solid phase may comprise hydrophilic components and/or water soluble components that may be at least partially dehydrated. In some embodiments, impurities present in a liquid phase may comprise hydrophobic components and/or water insoluble components. In some embodiments, impurities present in a liquid phase may comprise hydrophilic components and/or water soluble components. A hydrophilic component and/or water soluble component may be present in a liquid phase in an amount of less than about 5%, 4%, 3%, 2%, 1%, 0.5%, or 0.1% by weight of the liquid phase.

A method of the present invention may remove (e.g., dissolve or extract) water from a water soluble component, which may be present in the liquid cell culture media, and may provide a solidified component. In some embodiments, a method of the present invention comprises removing water from a biologic present in a liquid cell culture media and providing a solidified biologic (i.e., the biologic in a solid form). Water may also be removed from impurities (e.g., water soluble impurities) and provide a solidified impurity. A solidified component (e.g., a solidified biologic and/or impurity) may be present in any form such as, for example, a microparticle, nanoparticle, microsphere, or nanosphere. In some embodiments, the solidified component is amorphous (e.g., an amorphous particle). In some embodiments, at least a portion of the solidified component is amorphous, so the solidified component may be partially amorphous. For example, a matrix of a solidified component may be amorphous, but molecules within the matrix (e.g., a salt) may be crystalline. In some embodiments, the solidified component is separated from any liquid and/or provided in the form of a powder. The process of removing water from a component (i.e., dehydrating a component) to provide a solid is referred to herein as "microglassification" and the solidified component may be referred to herein as a "microglassified" component. A microglassified component is not a precipitate. In some embodiments, a composition and/or method of the present invention does not include (i.e., is devoid of) a phase separating agent. Phase separation may occur during a microglassification method of the present invention, but the microglassified component is not formed by phase separation. A microglassified component may be dissolved back into the initial composition in which it was present (e.g., liquid cell culture media or an aqueous solution) and/or into an aqueous buffer.

According to some embodiments, a biologic is isolated or separated from a liquid cell culture medium in accordance with a method of the present invention. In some embodiments, the method comprises at least partially dehydrating the biologic. The method may simultaneously remove water from the liquid cell culture medium and preserve the biologic. Extracting water from the biologic may preserve the biologic and provide a solidified biologic (i.e., a microglassified biologic). One or more properties and/or functions of a biologic may be preserved and/or maintained with a microglassified biologic compared to the properties and/or functions of the biologic prior to microglassification and/or compared to the properties and/or functions of a control biologic that was not microglassified.

A biologic may be present in a liquid cell culture medium at a concentration of less than about 200, 175, 150, 125, 100, 90, 80, 70, 60, 50, 40, 30, 20, 10, 5, 1, 0.1, 0.05, or 0.01 mg/mL. In some embodiments, the biologic is present in a liquid cell culture medium at a concentration in a range of from about 0.01, 0.05, 0.1, 0.5, 1, or 5 mg/mL to about 10, 15, 20, 25, 30, 35, 40, 45, or 50 mg/mL. In some embodiments, the biologic is at least partially encapsulated in a cell present in the liquid cell culture medium.

As used herein "contact", "contacting", "contacted," and grammatical variations thereof, refer to bringing two or more materials (e.g., compositions, compounds, solvents, etc.) together to form a mixture. Contacting the two or more materials may be carried out by pouring, spraying, mixing, flowing, injecting, and/or the like the two materials or a portion thereof together. For example, contacting may comprise adding a solvent to a liquid cell culture media or adding a liquid cell culture media to a solvent. In some embodiments, two or more materials may be contacted during a membrane emulsification method and/or technique. Contacting may be carried out in a device such as, e.g., a mixer, homogenizer, and/or microfluidic device.

In some embodiments, contacting comprises bringing two or more materials (e.g., compositions, compounds, solvents, etc.) together in sufficient proximity such that, under suitable conditions, a desired reaction can be carried out (e.g., water can be removed from a component present in one of the materials). In some embodiments, a contacting step in a method of the present invention forms a mixture and the mixture may be one phase or two or more (e.g., 2, 3, or more) phases. In some embodiments, the mixture is a multi-phase composition in that the composition has two or more (e.g., 2, 3, 4, or more) phases. In some embodiments, a contacting step in a method of the present invention forms a two phase composition and/or an emulsion. In some embodiments, a contacting step in a method of the present invention forms a suspension (e.g., one or more liquid phases including a solid particle). In some embodiments, an emulsion is formed and the emulsion may be a water-in-oil emulsion, optionally comprising droplets with a diameter and/or smallest dimension of less than about 1000, 900, 800, 700, 600, 500, 400, 300, 200, 100, 50, 25, 10, 5 or 1 μm. In some embodiments, the mixture is a water-in-oil emulsion comprising droplets having a diameter and/or smallest dimension in a range of about 5, 10, 25, 50, 100, 200, 300, 400, or 500 μm to about 600, 700, 800, 900, or 1000 μm. In some embodiments, the mixture is a water-in-oil emulsion comprising droplets having a diameter and/or smallest dimension in a range of about 0.1, 0.5, 1, 2, 3, 4, or 5 μm to about 6, 7, 8, 9, 10, 11, 12, 13, 14, or 15 μm. In some embodiments, a contacting step in a method of the present invention forms a mixture (e.g., an emulsion) and a component present in one of the materials is at least partially dehydrated as a result of the contacting step and/or forming the mixture.

A liquid cell culture medium may be contacted with a dehydration composition that at least partially dehydrates a component (e.g., a biologic) present in the liquid cell culture medium. Upon contacting the dehydration composition and liquid cell culture medium, the dehydration composition may be present in a concentration sufficient to at least partially dehydrate a component present in the liquid cell culture medium. In some embodiments, the dehydration composition comprises a solvent (e.g., an organic solvent) that removes water from a component (e.g., biologic). Exemplary organic solvents include, but are not limited to, alcohols such as, e.g., an alcohol having 1-20 carbons (i.e., a C1-C20 alcohol) or a C4-C20 alcohol, ester containing compounds (e.g., a C1-C20 ester containing compound such as, e.g., ethyl acetate, butyl acetate, triacetin, isobutyl acetate, isopropyl acetate, methyl acetate, propyl acetate, and/or butyl lactate), acetic acid, acetone, anisole, tert butyl methyl ether, cumene, dimethyl sulfoxide, diethyl ether, ethyl formate, formic acid, alkanes (e.g., heptane, pentane, etc.), and/or methylethylketone.

In some embodiments, a dehydration composition comprises a C1, C2, C3, C4, C5, C6, C7, C8, C9, C10, C11, C12, C13, C14, C15, C16, C17, C18, C19, and/or C20 alcohol and/or a C1, C2, C3, C4, C5, C6, C7, C8, C9, C10, C11, C12, C13, C14, C15, C16, C17, C18, C19, and/or C20 ester containing compound. In some embodiments, the alcohol is selected from methanol; ethanol; propanol (e.g., 1-propanol; 2-propanol); butanol (e.g., 1-butanol; 2-butanol); 2-methyl-1-proponal; 2-methyl-2-propanol; tert-butanol; pentanol (e.g., 1-pentanol, 3-methyl-1-butanol, 2,2-dimethyl-1-propanol, cyclopentanol); hexanol (e.g., 1-hexanol); cyclohexanol; heptanol (e.g., 1-heptanol); octanol (e.g., 1-octanol); nonanol (e.g., 1-nonanol); decanol (e.g., 1-decanol); 2-propen-1-ol; benzyl alcohol; phenylmethanol; diphenylmethanol; undecanol; dodecanol; propyldecanol; butadecanol; pentadecanol; hexadecanol (e.g., 1-hexadecanol); and/or triphenylmethanol. In some embodiments, a dehydration composition does not comprise a C10 alcohol (e.g., 1-decanol). In some embodiments, the ester containing compound may be formed from an acid and a C1-C20, C1-C10, C1-C8, C1-C6, or C1-C4 alcohol. In some embodiments, a dehydration composition comprises an isomer of a linear alcohol (e.g., 2-octanol, 3-pentanol, 4-decanol), a derivative of a linear alcohol or their isomer (e.g., octyldodecanol, neopentyl alcohol), a di, tri, or quad hydroxylated materials (e.g., 1,4-butanediol, glycerin), an unsaturated alcohol (e.g., a cyclic, olefinic or alkynyl alcohol such as e.g., cyclohexanol, geraniol, oleic alcohol), and/or an alcohol incorporating an internal and/or external heteroatoms (e.g., polyethylene glycols, polypropylene glycols, lactates, etc.).

One or more (e.g., 1, 2, 3, 4, or more) solvents may be present in a dehydration composition of the present invention. For example, in some embodiments, at least two alcohols are present in a dehydration composition (e.g., 1-pentanol and 1-hexadecanol), at least two ester containing compounds (e.g., ethyl acetate and triacetin), or at least one alcohol (e.g., 1-pentanol) and one ester containing compound (e.g., ethyl acetate). When two or more solvents are present in a dehydration composition, they may be present in any suitable ratio. In some embodiments, a dehydration composition comprises two solvents that are present in the composition in a ratio (by volume or weight) of about 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20.

A solvent (e.g., organic solvent) present in a dehydration composition of the present invention may have a solubility for water of about 0.05%, 1%, 2%, or 5% to about 10%, 12%, 15%, 20%, 25%, 30%, 35%, 40%, 45%, or 50% w/w. In some embodiments, the organic solvent has a solubility for water of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% w/w. A solvent (e.g., an organic solvent) may have an interfacial tension with water less than about 55 mN/m. In some embodiments, a solvent present in a dehydration composition of the present invention has an interfacial tension with water that is less than about 55, 50, 45, 40, 35, 30, 25, 20, 15, 10, 9, 8, 7, 6, 5, 4, 3, 2, or 1 mN/m. In some embodiments, a solvent present in a dehydration composition of the present invention has an interfacial tension with water in a range of about 1, 2, 3, 4, or 5 to about 6, 7, 8, 9, or 10. In some embodiments, a solvent present in a dehydration composition of the present invention is miscible with an emulsification solvent.

In some embodiments, a dehydration composition of the present invention consists of an organic solvent (e.g., an alcohol). In some embodiments, the dehydration composition consists of two or more C1-C20 alcohols. In some embodiments, a dehydration composition of the present invention comprises an organic solvent in an amount of about 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% by weight of the dehydration composition.

A dehydration composition may comprise one or more (e.g., 1, 2, 3, 4, 5, or more) additives (e.g., stabilizers, surfactants, tonicity agents, salts, sugars, antimicrobial agents, antioxidants, etc.). Exemplary additives (e.g., surfactants, antimicrobial agents, antioxidants, etc.) include, but are not limited to, those described above. In some embodiments, an additive is present in a dehydration composition at a concentration of about 0.01%, 0.1%, or 0.5% to about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, or 35% by weight of the dehydration composition. In some embodiments, the dehydration composition comprises a surfactant and/or a sugar. In some embodiments, a surfactant may be present in a dehydration composition in an amount of about 30% or less by weight of the dehydration composition such as, e.g., about 25%, 20%, 15%, 10%, 5%, or less by weight of the dehydration composition. In some embodiments, an antimicrobial agent may be present in a dehydration composition in an amount of about 1% or less by weight of the dehydration composition such as, e.g., about 0.5%, 0.1%, or less by weight of the dehydration composition. In some embodiments, an antioxidant may be present in a dehydration composition in an amount of about 2.5% or less by weight of the dehydration composition such as, e.g., about 2%, 1.5%, 1%, 0.5%, 0.1%, or less by weight of the dehydration composition.

In some embodiments, a dehydration composition comprises at least one alcohol selected from benzyl alcohol, 1-propanol, 1-butanol, tert-butyl, sec-butyl, 1-pentanol, 1-hexanol, 1-heptanol, 1-octanol, 1-nonanol, 1-decanol, 1-undecanol, 1-dodecanol, propyldecanol, butadecanol, pentadecanol, and hexadecanol, and/or at least one solvent selected from water, triacetin, benzyl alcohol, acetic acid, acetone, anisole, 2-butanol, butyl acetate, tert butyl methyl ether, cumene, dimethyl sulfoxide, ethanol, ethyl acetate, diethyl ether, ethyl formate, formic acid, heptane, isobutyl acetate, isopropyl acetate, methyl acetate, 3-methyl-1-butanol, methylethylketone, 2-methyl-1-propanol, pentane, 2-propanol, propyl acetate, and tert-butanol. Further exemplary solvents that may be present in a dehydration composition include, but are not limited to, alkanes such as, e.g., an alkane having 1-20 carbon atoms (i.e., a C1-C20 alkane) or a C4-C20 alkane (e.g., propane, pentane, hexane, etc.); alcohols (e.g., a C5-C14 alcohol); acetates; esters; ethers; carboxylic acids; (poly)heteroatomic cyclic, acyclic, linear or branched molecules; and/or lactates. In some embodiments, a dehydration composition includes a solvent that includes a carbon, nitrogen, and/or sulfur atom.

A method of the present invention may comprise contacting a liquid cell culture media and one or more (e.g., 1, 2, 3, 4, or more) dehydration compositions. Accordingly, a method of the present invention may comprise contacting a liquid cell culture media and one or more (e.g., 1, 2, 3, 4, or more) solvents such as, e.g., a first organic solvent, second organic solvent, etc. When two or more dehydration compositions are used in a method of the present invention, the solvent present in the compositions may be the same or different. In some embodiments, a solvent present in a dehydration composition may be more volatile than a solvent in an immediately prior dehydration composition and/or may be a volatile organic compound (e.g., has a boiling point from about 0, 50, or 100° C. to about 150, 200, or 260° C.). In some embodiments, a dehydration composition and an at least partially dehydrated component may be contacted one or more (e.g., 1, 2, 3, 4, 5, or more) times.

A batch or inline process may be used to contact the liquid cell culture media with one or more dehydration compositions. In some embodiments, a method of the present invention comprises contacting a liquid cell culture media and first dehydration composition to form a mixture, then contacting the mixture and a second dehydration composition. In some embodiments, a method of the present invention comprises contacting a liquid cell culture media and first dehydration composition to form a mixture, separating an at least partially dehydrated component from the mixture, and contacting the at least partially dehydrated component with a second dehydration composition.

A solvent present in a dehydration composition may form an interface with a liquid cell culture medium and/or aqueous composition. In some embodiments, a solvent present in a dehydration composition is not miscible with water. In some embodiments, a solvent present in a dehydration composition that is used first to dehydrate a component (i.e., a first dehydration composition or first organic solvent) is immiscible with water and/or forms an interface with water, and the solvent is at least partially water soluble. In some embodiments, a solvent present in a dehydration composition that is used after a first dehydration composition (e.g., a second or third dehydration composition or second or third organic solvent) is not miscible with water.

Contacting a dehydration composition and liquid cell culture media and/or forming a mixture may comprise reducing the water content of a component (e.g., biologic) present in the mixture by at least about 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. In some embodiments, the water content of the component is reduced by about 5%, 10%, 15%, 20%, 25%, 30%, or 35% to about 40%, 45%, 50%, 55%, 60%, 65%, 70%, 75%, 80%, 85%, 90% or 95% after a contacting step of the present invention.

A mixture comprising a dehydration composition and liquid cell culture medium may have a water activity of less than about 0.99, 0.98, 0.95, 0.9, 0.85, 0.8, 0.75, 0.7, 0.65, 0.6, 0.55, 0.5, 0.45, 0.4, 0.35, 0.3, 0.25, 0.2, 0.15, or 0.1. In some embodiments, the mixture has a water activity in a range of about 0.1, 0.15, 0.2, 0.25, 0.3, 0.35, 0.4, 0.45, or 0.5 to about 0.55, 0.6, 0.65, 0.7, 0.75, 0.8, 0.85, 0.9, or 0.95. In some embodiments, the mixture has a fractional water saturation of less than about 0.95, 0.9, 0.85, 0.8, 0.75, 0.7, 0.65, 0.6, 0.55, 0.5, 0.45, 0.4, 0.35, 0.3, 0.25, 0.2, 0.15, or 0.1. In some embodiments, the mixture has a fractional water saturation in a range of about 0.1, 0.15, 0.2, 0.25, 0.3, 0.35, 0.4, 0.45, or 0.5 to about 0.55, 0.6, 0.65, 0.7, 0.75, 0.8, 0.85, 0.9, or 0.95. For example, in some embodiments, a mixture comprising a protein may have a fractional water saturation of about 0.95 or less. In some embodiments, a mixture comprising a salt may have a fractional water saturation of about 0.5 or less.

An at least partially dehydrated component (e.g., biologic) may have a water content of about 99%, 98%, 95%, 90%, 85%, 80%, 75%, 70%, 65%, 60%, 55%, 50%, 45%, 40%, 35%, 30%, 25%, 20%, 15%, 10%, 5%, 1%, or 0% after being contacted with one or more dehydration compositions. In some embodiments, an at least partially dehydrated component (e.g., biologic) has a water content in a range of about 0%, 0.5%, 1%, 5%, 10%, 15%, 20%, or 25% to about 30%, 35%, 40%, 45%, 50%, 55%, 60%, 65%, 70%, or 75% after being contacted with one or more dehydration compositions. In some embodiments, an at least partially dehydrated component (e.g., biologic) has a water content in a range of about 0%, 0.5%, 1%, 2%, 3%, or 4% to about 5%, 6%, 7%, 8%, 9%, or 10% after being contacted with one or more dehydration compositions. In some embodiments, an at least partially dehydrated component (e.g., biologic) has a water activity of about 0.986, 0.98, 0.95, 0.9, 0.85, 0.8, 0.75, 0.7, 0.65, 0.6, 0.55, 0.5, 0.45, 0.4, 0.35, 0.3, 0.25, 0.2, 0.15, 0.1, 0.05, or 0 after being contacted with one or more dehydration compositions. In some embodiments, an at least partially dehydrated component (e.g., biologic) has a water activity of in a range of about 0, 0.05, 0.1, 0.15, 0.2, 0.25, or 0.3 to about 0.35, 0.4, 0.5, 0.6, 0.7, 0.8, or 0.9 after being contacted with one or more dehydration compositions.

In some embodiments, after contacting an initial dehydration composition and liquid cell culture medium, an at least partially dehydrated component has a water content of less than about 60% and/or in a range of about 1%, 5%, 10%, 15%, 20%, or 25% to about 30%, 35%, 40%, 45%, 50%, 55%, 60%, 65%, or 70%. In some embodiments, after contacting an at least partially dehydrated component and a subsequent (e.g., second) dehydration composition, which may be the same as the initial dehydration composition or different, the at least partially dehydrated component has a water content of less than about 45% and/or in a range of about 0.5%, 1%, 5%, 10%, 15%, or 20% to about 25%, 30%, 35%, 40%, 45%, 50%, 55%, 60%, 65%, or 70%.

The contacting step in a method of the present invention may be carried out at a temperature in a range of about −50, −20, −10, 0, 4, 10, 15, or 20° C. to about 25, 20, 35, 40, 45, or 50° C. In some embodiments, the contacting step in a method of the present invention is carried out at room temperature and/or atmospheric pressure. In some embodiments, a method of the present invention may comprise a device, step, and/or composition as described in U.S. Pat. No. 8,013,022, which is incorporated herein by reference in its entirety.

In some embodiments, upon contacting a dehydration composition (e.g., an organic solvent) and the liquid cell culture medium and/or forming a mixture comprising the dehydration composition and liquid cell culture medium, a suspension may be formed, the suspension comprising a component (e.g., a biologic) in the form of a solid suspended in a liquid (e.g., the mixture). Contacting a dehydration composition and liquid cell culture medium to provide a mixture and forming an at least partially dehydrated component in the mixture may be performed substantially simultaneously. "Substantially simultaneously" as used herein in reference to at least partially dehydrating a component refers to at least partially dehydrating a component immediately upon contact with a dehydration composition or in less than about 1 minute from initial contact with the dehydration composition. In some embodiments, forming an at least partially dehydrated component in the mixture is achieved within about 100 minutes or less (e.g., about 90, 60, 30, 15, 10, 5, or 1 or less) after initial contact of a dehydration composition and the liquid cell culture medium.

In some embodiments, an at least partially dehydrated component (e.g. biologic) having a water content of less than about 60%, 55%, 50%, 45%, 40%, 35%, 30%, 25%, 20%, 15%, 10%, or 5% may be achieved within less than about 10, 9, 8, 7, 6, 5, 4, 3, 2, or 1 minutes or less than about 50, 40, 30, 20, 10, 5, 1, 0.5, or 0.1 seconds. In some embodiments, an at least partially dehydrated component (e.g. biologic) having a water content of less than about 60%, 55%, 50%, 45%, 40%, 35%, 30%, 25%, 20%, 15%, 10%, or 5% may be achieved within about 0.01, 0.05, 0.1, or 0.5 seconds to about 1, 2, 3, 4, 5, 6, 7, 8, 9, or 10 seconds.

Contacting a dehydration composition and liquid cell culture medium may comprise at least partially lysing cells present in the liquid cell culture medium and/or at least partially dissolving lipids and/or the cell membranes present in the liquid cell culture medium.

According to some embodiments, contacting two different compositions (e.g., a dehydration composition and liquid cell culture medium, or a solvent and a composition comprising an at least partially dehydrated component) comprising mixing them together. Mixing may be accomplished by any methods known in the art such as, e.g., vortexing, stirring, static mixing, homogenizing, extruding, pumping, injecting, adding one composition to another, spraying one composition into another, and/or spraying the compositions together to form a mixture. Mixing may form an emulsion and/or air may be incorporated into a mixture to form an emulsion. One composition may be added to another using a slow addition, fast addition, or total addition and mixing may be accomplished with low shear and/or high shear (e.g., about 1-10000000/s). When the two different compositions comprise an aqueous composition and a hydrophobic composition (e.g., a composition comprising an organic solvent) the aqueous composition may be added to the hydrophobic composition or vice versa. In some embodiments, the two different compositions are contacted prior to mixing and/or are contacted in a mixer. Exemplary mixers include, but are not limited to, high pressure homogenizers, rotor-stator homogenizers, impellars, pipeline mixers (turbulent and laminar), static mixers, in-line mixers, and/or microfluidic devices (e.g., a microfluidic device including a cross junction). In some embodiments, the mixer is inline such as, e.g., an inline homogenizer. In some embodiments, the mixer is a device (e.g., a microfluidic device) and two different compositions may be added or injected into the device to thereby mix the two different compositions together. Forming an at least partially dehydrated component may comprise mixing (e.g., homogenizing) the mixture.

In some embodiments, two different compositions that form a mixture and/or a composition comprising an at least partially dehydrated component may be mixed, such as in a batch process, at a ratio that is a volume ratio of the two different compositions. For example, for a first composition and a second composition that are to be contacted in a batch process to form a mixture, the volume ratio may be a volume to be mixed for the first composition to a volume to be mixed of the second composition. In some embodiments, two different compositions that form a mixture and/or a composition comprising an at least partially dehydrated component may be mixed, such as in an inline process, at a ratio based on the feed rate of the two different compositions. For example, for a first composition and a second composition that are to be contacted in an inline process to form a mixture, the ratio may be a feed rate (e.g., flow rate) for the first composition during the contacting step to a feed rate (e.g., flow rate) for the second composition during the contacting step.

In some embodiments, two different compositions that form a mixture and/or a composition comprising an at least partially dehydrated component may be mixed (e.g., homogenized) at a feed rate (e.g., flow rate) in a range of about 1, 5, 10, 25, 50, 75, or 100 mL/min to about 150, 250, 500, 1,000, 1,500, or 2,000 mL/min. In some embodiments, two different compositions that form a mixture and/or a composition comprising an at least partially dehydrated component may be mixed (e.g., homogenized) at a feed rate in a range of about 1, 5, 10, 25, 50, 75, or 100 L/hour to about 150, 250, 500, 1,000, 1,500, 2,000, 2,500, 3,000, 3,500, or 4,000 L/hour. The feed rate for each composition may be the same or different.

In some embodiments, two different compositions that form a mixture and/or a composition comprising an at least partially dehydrated component may be contacted and/or combined with a given feed volume ratio. The two different compositions may include an aqueous composition (e.g., a liquid cell culture medium and/or composition comprising water) that provides an aqueous phase, and a solvent containing composition (e.g., a hydrophobic composition) that provides a solvent phase. In some embodiments, the two different compositions may be contacted and/or combined with a feed volume ratio of about 0.1:100, 0.2:100, 0.3:100, 0.4:100, 0.5:100, 0.6:100, 0.7:100, 0.8:100, 0.9:100, 1:100, 1.5:100, 2:100, 2.5:100, 3:100, 3.5:100, 4:100, 4.5:100, 5:100, 5.5:100, 6:100, 6.5:100, 7:100, 7.5:100, 8:100, 8.5:100, 9:100, 9.5:100, 10:100, 11:100, 12:100, 13:100, 14:100, 15:100, 16:100, 17:100, 18:100, 19:100, 20:100, 21:100, 22:100, 23:100, 24:100, or 25:100 (aqueous composition:solvent containing composition). In some embodiments, the two different compositions that form a mixture and/or a composition comprising an least partially dehydrated component may be contacted and/or combined with a feed volume ratio in a range of about 0.1:100, 0.3:100, 0.5:100, 0.7:100, or 1:100 to about 2:100, 4:100, 6:100, 8:100, 10:100, 12:100, 14:100, 16:100, 18:100, 20:100, 22:100, or 25:100.

In some embodiments, an emulsification solvent (or composition comprising the same) may be contacted and/or combined with a liquid cell culture medium with a feed volume ratio of about 0.1:1, 0.2:1, 0.3:1, 0.4:1, 0.5:1, 0.6:1, 0.7:1, 0.8:1, 0.9:1, 1:1, 1.5:1, 2:1, 2.5:1, 3:1, 3.5:1, 4:1, 4.5:1, or 5:1 (liquid cell culture medium:emulsification solvent).

An at least partially dehydrated component may be separated from a mixture and/or liquid phase using methods known to those of skill in the art. For example, an at least partially dehydrated component may be separated from a liquid phase by filtration (e.g., pressure filtration, tangential flow filtration, rotary filtration, centrifugal filtration, disc stack filtration, etc.), cyclone separation, sedimentation (e.g., sedimentation by acoustic resonance fields), evaporation, centrifugation, fluid bed drying, evaporative drying, thermal drying, freeze drying, atmospheric freeze drying, spray drying, spray freeze drying, microwave/IR drying, and/or sieving. In some embodiments, an at least partially dehydrated component may be separated from a liquid phase by a washing step and/or solvent exchange method, sedimentation and/or filtration step, and/or further dried (e.g., to remove water and/or a solvent) using air, vacuum, and/or, freeze drying step, and/or any combination thereof.

In some embodiments, a method of the present invention comprises washing an at least partially dehydrated component with a wash composition. A wash composition may comprise an organic solvent such as, e.g., an alcohol (e.g., a C1-C20 alcohol), alkane (e.g., a C4-C20 alkane), ester, and/or ether. Such organic solvents include, but are not limited to those, described above and/or an organic solvent may have solubility for water as described above. In some embodiments, an organic solvent in a wash composition is miscible with water. An organic solvent in a wash composition may be the same as or different than an organic solvent in a dehydration composition. In some embodiments, an organic solvent present in a wash composition may be a Class II or Class III residual solvent as classified by the Food & Drug Administration.

In some embodiments, an organic solvent present in a wash composition may be more volatile than an organic solvent a dehydration composition. In some embodiments, an organic solvent in a wash composition is a volatile organic compound (e.g., has a boiling point from about 0, 50, or 100° C. to about 150, 200, or 260° C.). In some embodiments, a wash composition may be used to wash away and/or remove a dehydration composition, emulsification solvent, organic solvent, and/or impurity. In some embodiments, an organic solvent present in a wash composition has a solubility for an emulsification solvent and/or for a solvent present in a dehydration composition.

According to some embodiments, a method of the present invention is a one step method in which a liquid cell culture medium is contacted to a dehydration composition to provide an emulsion and an isolated component (e.g., an at least partially dehydrated biologic). The contacting step in a one step method may be repeated one or more times (e.g., 1, 2, 3, 4, 5, or more times) with the same or a different dehydration composition. In some embodiments, a method of the present invention is a two step method that comprises a pre-emulsification step in which a liquid cell culture medium is contacted with an emulsification solvent to form an emulsion (e.g., a coarse emulsion) and the emulsion is subsequently contacted with a dehydration composition to provide an isolated component. Each of the contacting steps in a two step method may be repeated one or more times (e.g., 1, 2, 3, 4, 5, or more times) with the same or a different emulsification solvent and/or dehydration composition. The one step method or two step method may further comprise contacting the at least partially dehydrated component or a composition comprising the same with a wash composition that optionally includes an organic solvent that is more volatile than prior organic solvent(s) used in the method.

A method of the present invention may contact an emulsification solvent, dehydration composition, or wash composition with a liquid cell culture medium, an at least partially dehydrated component, or a composition comprising an at least partially dehydrated component for a period of time. The contact time for each of these steps may be for about 1, 5, 15, 30, 45, or 60 minutes or about 1, 2, 3, 4, 5, 6, 7, 8, 9, 10, 11, 12, 13, 14, 15, 16, 17, 18, 19, 20, 21, 22, 23, or 24 hours or more. In some embodiments, the contact time is about 1, 5, or 15 minutes to about 30, 45, or 60 minutes or about 1, 2, 3, 4, or 5 hours to about 6, 7, 8, 9, or 10 hours or more. In some embodiments, the time period in which an emulsification solvent is contacted to a liquid cell culture medium is less than the time period for which a dehydration composition and/or wash composition is contacted to an at least partially dehydrated component or a composition comprising the same.

A method of the present invention may comprise storing an isolated component such as, e.g., an isolated biologic or lipid. In some embodiments, a method of the present invention comprises purifying the isolated component. In some embodiments, a method of the present invention comprises hydrating an at least partially dehydrated component (e.g., biologic) and/or purifying the at least partially dehydrated component.

In some embodiments, a method of the present invention is devoid of a conventional lysing technique. Exemplarily conventional lysing techniques include, but are not limited to, multiple freeze/thaw cycles, sonication, high-pressure homogenization, grinding, and/or permeabilization of a cell membrane with a detergent and/or enzyme. In some embodiments, a liquid cell culture medium is not lysed (e.g., by physical disruption and/or permeabilization) prior to a first step of a method of the present invention. In some embodiments, a method of the present invention is devoid of a lysing step carried out with a one phase composition (i.e., a plurality of cells are present in a one phase composition). In some embodiments, a method of the present invention comprising a lysing step carried out with a two phase composition (i.e., a plurality of cells are present in a two phase composition such as, e.g., an emulsion and/or suspension).

In some embodiments, a liquid cell culture medium and/or a composition comprising an at least partially dehydrated component has a pH of greater than 7 such as, e.g., about 7.5, 8, 8.5, 9, 10, or more. In some embodiments, a liquid cell culture medium and/or a composition comprising an at least partially dehydrated component has a pH of less than 7 such as, e.g., about 6.5, 6, 5.5, 5, 4.5, 4, or less. In some embodiments, a liquid cell culture medium and/or a composition comprising an at least partially dehydrated component has a pH that is at least ±0.5, 1, 1.5, or 2 pH units away from the isoelectric point (pI) of the desired isolated component (e.g., the target biologic). In some embodiments, the pH of compositions comprising an at least partially dehydrated component in a method of the present invention varies by less than about ±2, 1.5, 1, or 0.5 pH units from the initial pH of the composition.

A method of the present invention may comprise collecting and/or recycling a composition and/or component thereof (e.g., a solvent and/or additive). In some embodiments, the composition and/or component thereof may be separated from an at least partially dehydrated component and optionally further processed by method including, but not limited to, distillation, absorption, precipitation, adsorption, filtration, dialysis, and/or the like to collect and/or recycle the composition and/or component thereof. In some embodiments, water and/or an impurity is removed from a collected and/or recycled composition and/or component thereof. In some embodiments, separating an at least partially dehydrated component from a liquid phase provides an isolated component (e.g. a lipid or steroid) in the liquid phase, which is separate from the at least partially dehydrated component. In some embodiments, water is removed from a collected and/or recycled composition and/or component thereof such as, e.g., by distillation. In some embodiments, an additive present in a collected and/or recycled composition and/or component thereof is removed such as, e.g., by a chemical separation method (e.g., filtration).

According to some embodiments of the present invention provided is a composition comprising a plurality of solid particles (e.g., microparticles). The solid particles may be amorphous and/or crystalline. In some embodiments, a plurality of solid particles comprises amorphous particles. In some embodiments, a plurality of solid particles may comprise crystalline particles such as, e.g., when small molecules (e.g., salts) are present that can be crystalized. In some embodiments, the composition may be provided and/or obtained following separation of the solid particles from a liquid phase. The plurality of solid particles may be uniform in size or may be polydisperse. In some embodiments, at least a portion of the plurality of solid particles have a size that is within about ±5%, 10%, 15%, 20%, 25%, 50%, 75%, 100%, 150%, 200% or more of the average particle size. In some embodiments, the composition comprises discrete particles. In some embodiments, the composition comprises aggregations of a biologic in an amount less than about 50%, 40%, 30%, 25%, 20%, 15%, 10%, 5%, 4%, 3%, 2%, or 1% by weight of the biologic.

In some embodiments, at least a portion of the plurality of solid particles in a composition of the present invention are solid biologic particles. In some embodiments, a composition comprising a plurality of solid particles comprises at least about 5%, 10%, 15%, 20%, 25%, 30%, 35%, 40%, 45%, 50%, 55%, 60%, 65%, 70%, 75%, 80%, 85%, 90%, 95%, 97%, or 100% solid biologic particles by weight of the composition. In some embodiments, the composition comprises one or more (e.g., 1, 2, 3, 4, or more) impurities such as, e.g., water soluble components that may be at least partially dehydrated. Impurities may be present in a composition comprising a plurality of solid particles in an amount of about 5%, 10%, 15%, 20%, 25%, 30%, 35%, 40%, 45%, 50%, 55%, 60%, 65%, 70%, 75%, 80%, 85%, 90%, 95%, 97%, or more by weight of the composition. In some embodiments, water insoluble components (e.g., lipids) may be present in a composition comprising a plurality of solid particles in an amount less than about 60%, 55%, 50%, 45%, 40%, 35%, 30%, 25%, 20%, 15%, 10%, or 5% by weight of the composition.

A method of the present invention may preserve a component present in a liquid cell culture medium. The component may be preserved and/or isolated from a liquid cell culture medium at multiple points in downstream purification of the medium, which may eliminate or reduce process flow interruption (e.g., due to instrument downtime) and/or may allow for increased production and/or yield of the isolated component such as, e.g., compared to a method of freezing, lyophilizing, and/or spray-drying the same component. In some embodiments, a method of the present invention achieves a yield of about 0.1, 0.5, 5, 10, 25, or 50 g/L. In some embodiments, a method of the present invention achieves a yield in a range of about 0.1, 1, 5, or 10 g/L to about 15, 20, 25, 30, 40, or 50 g/L. In some embodiments, a method of the present invention may reduce (e.g., by at least about 5% or 95% or more) storage and/or transportation volumes and/or weights for an isolated component (e.g., a microglassified biologic). In some embodiments, a method of the present invention provides an isolated component that can maintain one or more properties and/or functions and/or a desired activity level even after exposure to a temperature fluctuation of ±5, 10, 15, 20, or 25° C. or more.

In some embodiments, one or more properties and/or functions of a component (e.g., a biologic) may be preserved and/or maintained after formation of a solid biologic in accordance with a method of the present invention (i.e., a microglassification method) compared to the one or more properties and/or functions of the component prior to the method and/or compared to the one or more properties and/or functions of a control component. For example, in some embodiments, an at least partially dehydrated biologic may have an activity, optionally upon dissolution in a solution (e.g., an aqueous solution), that is within ±60%, 55%, 50%, 45%, 40%, 35%, 30%, 25%, 20%, 15%, 10%, or 5% of the activity of the biologic prior to a method of the present invention and/or in the absence of a method of the present invention (e.g., the activity of a control component). In some embodiments, an at least partially dehydrated biologic may have an activity, optionally upon dissolution in a solution, that is increased (e.g., by at least about 5% or more) compared to the activity of the same biologic that is frozen, lyophilized, and/or spray dried and optionally subsequently dissolved in a solution. In some embodiments, at least about 70%, 75%, 80%, 85%, 90%, 95%, 97%, 98%, 99%, or more of the activity of an at least partially dehydrated component of the present invention is retained compared to the activity of a control component (i.e., a component that is devoid of a method of the present invention) and/or the component prior to a method of the present invention. In some embodiments, a method of the present invention may provide an at least partially dehydrated biologic having comparable or improved flowability compared to the flowability of the same biologic that is frozen, lyophilized, and/or spray dried.

In some embodiments, the structure (e.g., primary, second, and/or tertiary) of a component (e.g., a biologic) may be preserved and/or maintained after formation of a solid biologic in accordance with a method of the present invention. In some embodiments, an at least partially dehydrated biologic having a folded structure may not unfold during a method of the present invention. In some embodiments, an at least partially dehydrated biologic having a folded structure may have a difference in structure of less than about 50%, 45%, 40%, 35%, 30%, 25%, 20%, 15%, or 5%.

An at least partially dehydrated component of the present invention may have an increased shelf life compared to the shelf life of the same component in the absence of a method of the present invention and/or compared to the shelf life of the same component following, freezing, lyophilization, and/or spray drying. "Shelf life" as used herein refers to the length of time a component maintains an activity at or above a certain level. In some embodiments, an at least partially dehydrated component of the present invention has a shelf life of at least 1, 2, 3, 4, 5, 6, 7, 8, 9, 10, 11, 12 or more weeks, months, and/or years when stored at a temperature of about 2, 4, 10, 15, or 20° C. to about 25, 20, 35 or 40° C., optionally at about 4° C. or 25° C.±5° C. In some embodiments, an at least partially dehydrated component of the present invention has a shelf life of at least 1, 2, 3, 4, 5, 6, 7, 8, 9, 10, 11, 12 or more weeks, months, and/or years when stored at a temperature of about 2° C. to about 8° C. or at about 5° C.±3° C. In some embodiments, a method of the present invention increases the amount of time an isolated component can be separated from a cell and/or cell culture medium without being purified compared to the amount of time for the same component that has been frozen, lyophilized, and/or spray dried. For example, in some embodiments, a composition of the present invention comprising a plurality of isolated microglassified components may remain under storage conditions (e.g., at a temperature of about 4, 10, 15, or 20° C. to about 25, 20, 35 or 40° C.) for at least 1, 2, 3, 4, 5, 6, 7, 8, 9, 10, 11, 12 or more weeks, months, and/or years without further purification and optionally without an activity loss greater than 20%.

In some embodiments, a method of the present invention reduces the time to achieve a given quantity of an isolated component compared to a different method for isolating the same quantity of the component. For example, in some embodiments, a method of the present invention may reduce the amount of time from cell culture to preservation and/or purification for a biologic compared to a different method (e.g., freezing, lyophilizing, and/or spray-drying) for preserving and/or purifying the same biologic in the same quantity. In some embodiments, a method of the present invention may achieve the same or an increased amount of an isolated component, optionally in less time, compared to a different method for isolating the component. In some embodiments, a method of the present invention provides for a biologic to be preserved quickly, optionally in less time than a different method (e.g., freezing, lyophilizing, and/or spray-drying), and the preserved biologic may then be purified immediately or stored and purified on demand.

A method of the present invention may comprise and/or be a continuous and/or inline process. In some embodiments, a method of the present invention may comprise and/or be a batch process. In some embodiments, a method of the present invention is continuous and/or inline with a cell culture step and/or method and/or is continuous and/or inline with a purification step and/or method for a component (e.g., a biologic). In some embodiments, a method of the present invention is continuous in that for a total volume of liquid cell culture medium in accordance with embodiments of the present invention only a portion (e.g., less than about 50%) of the total volume undergoes one or more steps of the method at a given time.

The present invention is explained in greater detail in the following non-limiting examples.

EXAMPLES

Example 1

Using a dehydration method, referred to herein as microglassification, dry, dense particles of lysozyme were produced. The lysozyme particles were produced by adding 0.16 mL of 100 mg/mL lysozyme solution to 0.8 mL pentanol (used here as an emulsification solvent) and vortexed briefly to form a coarse emulsion. The emulsion was then passed through an Avanti Lipids hand extruder 10-20 times to form a finer emulsion. This emulsion was then added to a stirred volume of pentanol (7 mL) (used here as a dehydration composition), which immediately dehydrated the aqueous droplets resulting in a suspension of partially dehydrated particles. The extruding process was repeated a total of 3 times to dehydrate a total of 0.48 mL of aqueous solution in that volume of pentanol. The suspension is shown in FIG. 1. The particles were then collected by filtration through a 0.2 micron filter. As can be seen from FIG. 1, using an emulsion solvent results in a suspension of small, relatively uniform particles.

Prior experiments with microglassifed lysozyme (see, e.g., Aniket, Gaul D A, Bitterfield D L, Su J T, Li V M, Singh I, et al. Enzyme Dehydration Using Microglassification™ Preserves the Protein's Structure and Function. J Pharm Sci. 2015 February; 104(2):640-51) have demonstrated that, when compared to lyophilized lysozyme, both samples lost activity after the first month of storage 40° C., but there was no difference between the MICROGLASSIFIED™ lysozyme and lyophilized lysozyme at three months.

Example 2

A micropipette dehydration technique has been used to study the kinetics of droplet dissolution or dehydration. This technique allows real-time observation of droplet dissolution, and therefore real-time observation of any phase changes. This technique also permits calculation of final particle density or protein concentration. As a tool for measuring two-phase microsystems, the micropipette technique has shown that gas-liquid and liquid-liquid systems follow the kinetics of the Epstein-Plesset model, which depends on the solubility and diffusion of the dissolving component in the surrounding phase:

$$\frac{dR}{dt} = -\frac{c_s}{\rho}(1-f)\left(\frac{1}{R} + \frac{1}{\sqrt{\rho Dt}}\right)$$

where R=droplet radius, cs=the solubility of the dissolving component, r=the density of the dissolving component, D=diffusion coefficient of the dissolving component, and f=saturation fraction of the surrounding medium. Once these parameters are known (or measured using the micropipette), the dissolution profile of any other droplet in the system can be predicted. Kinetic parameters measured for a single droplet can then be extrapolated to predict the kinetics for any droplet size in any other solvent system.

Figure 2:
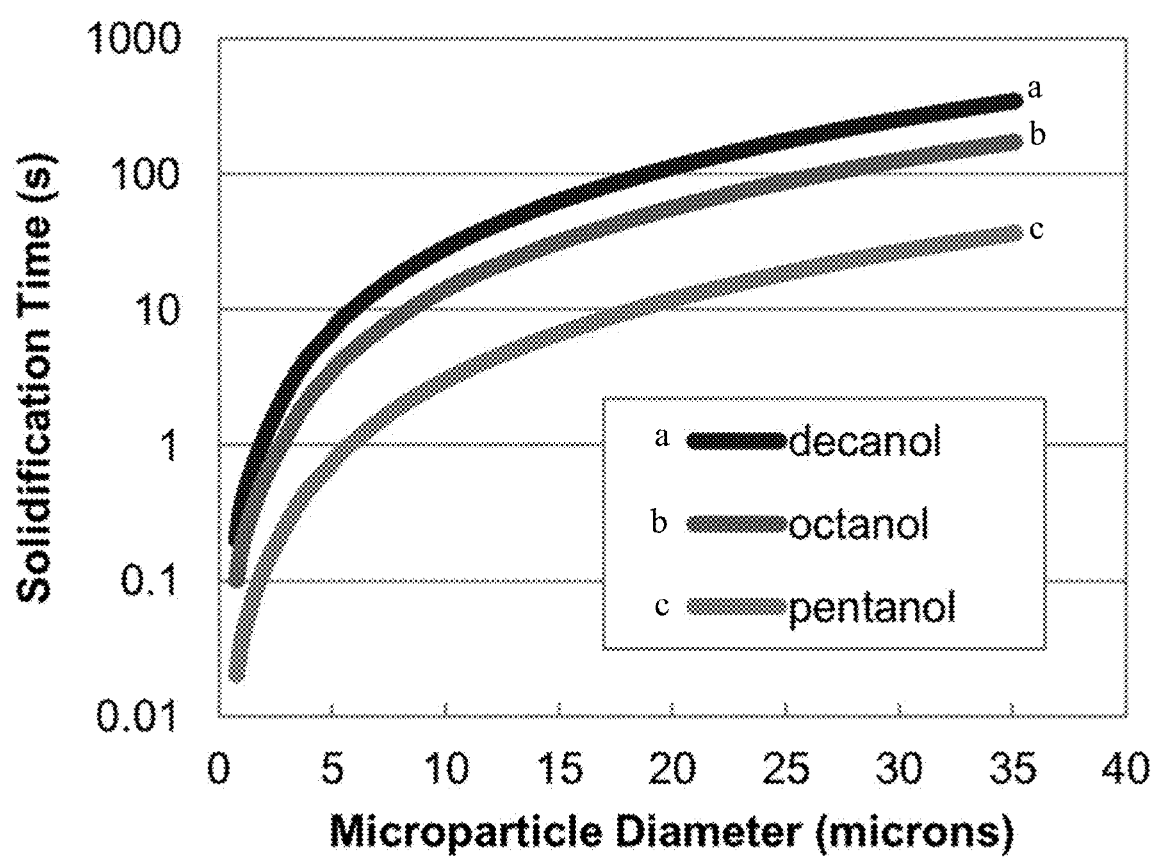
FIG. 2 is a graph showing predicted solidification times based on the Epstein-Plesset equation, assuming 50 mg/mL, with f=0.3 to account for bulk addition of water. Actual solidification time can be increased due to mixing.

The dehydration rate of a protein solution closely follows that of a water droplet (or salt solution droplet), and is a function of droplet size, dehydration solvent, and water saturation fraction. The influence of each of these factors has been discussed (Rickard D L, *Biophys J.* 2010; 98(6):1075-84; Duncan P B, *Langmuir.* 2004 Mar. 30; 20(7):2567-78; Bitterfield D L, *Langmuir.* 2016 Dec. 6; 32(48):12749-59; and Su J T, *J Chem Phys.* 2010; 132(4):44506) and can be used to predict the required residence time (and therefore flow rate) in a homogenizer or other mixer. For example, FIG. 2 shows the predicted solidification times in various dehydration solvents as a function of final particle size. For particles the size range of 2-20 μm, for example, dehydration is complete within 0.1 seconds to 10 seconds.

The resulting particles can be separated from the drying solvent, and solvent disposal or reuse can be accomplished. A drying solvent used in the method can be recycled. For example, in a microglassification method, a 200 L batch of Microglassified protein may require about 14,000 L of drying solvent (e.g., octanol). Compared to freeze-drying or spray-drying, Microglassification™ offers higher throughput and potentially easier scaling. A small fermentation batch of 200 L would take 220-300 hours to process on a lab-scale spray-dryer (~15 mL/min feed rate). A pilot-scale dryer provides only a 4× improvement (50 mL/min). Initial tests with a laboratory-scale in-line homogenizer using a dehydration microglassification method reached protein feed rates of about 2 mL/min. However, IKA (and other vendors) provides standard scaled homogenizers that maintain similar shear rates, allowing 2500× improvements in scale, or 300 L/hr. A 20,000-L fermentation batch could be processed by a single homogenizer unit within about 60 hours.

Many Microglassification™ studies have been conducted using a small-batch homogenization process, producing mg quantities of Microglassifed product at a time. To evaluate the feasibility of scale-up, the process was tested using an inline homogenizer. Bovine gamma globulin (BGG) was used as a model protein, as the majority of BGG is comprised of immunoglobulin proteins that are commonly manufactured for multiple therapeutic purposes. Total flow rates reaching 180 mL/min were obtained and flow rate ratios of 1:26 to 1:132 used with no detrimental effect on size distribution. These high flow rates result in the Microglassification™ of grams of protein within minutes—a significant stride in feasible scalability.

Figure 3:
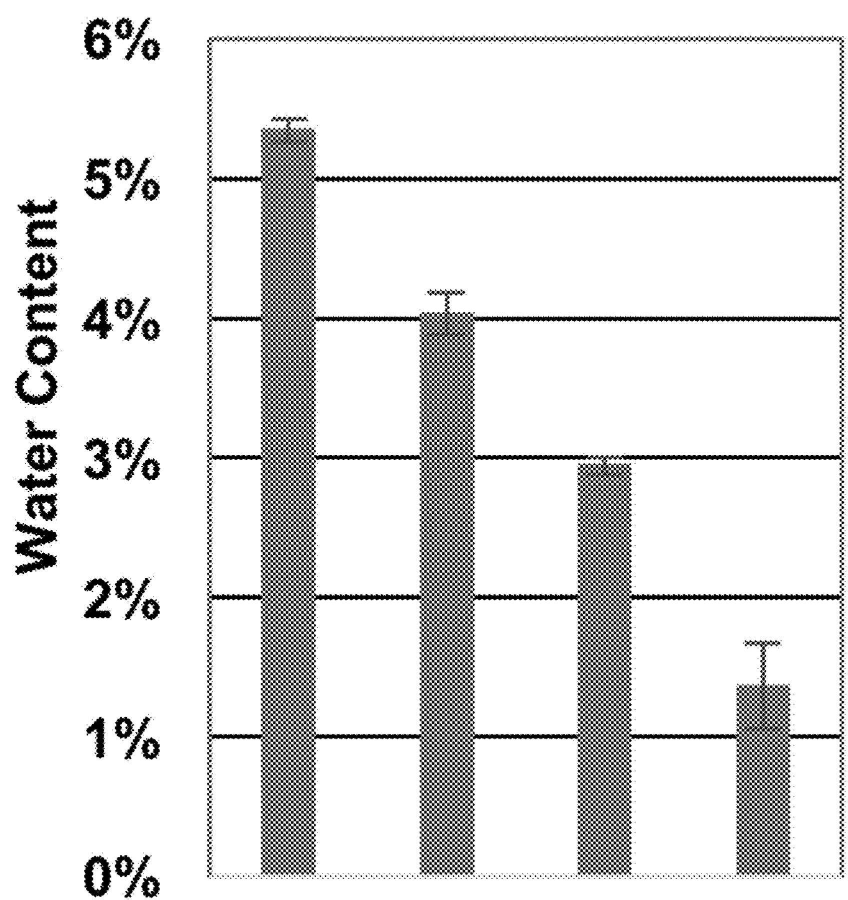
FIG. 3 is a graph showing residual water content in Microglassified™ bovine gamma globulin (BGG) batches produced using 4 different processing schemes.

Moisture content of the microglassified BGG was determined via Karl Fischer (KF) analysis and was found to be comparable to the moisture content of spray-dried protein (4-9%) (FIG. 3). As shown in FIG. 3, the final water content in the dehydrated protein was modifiable by adjusting the manner in which the final protein was isolated.

Figure 4:
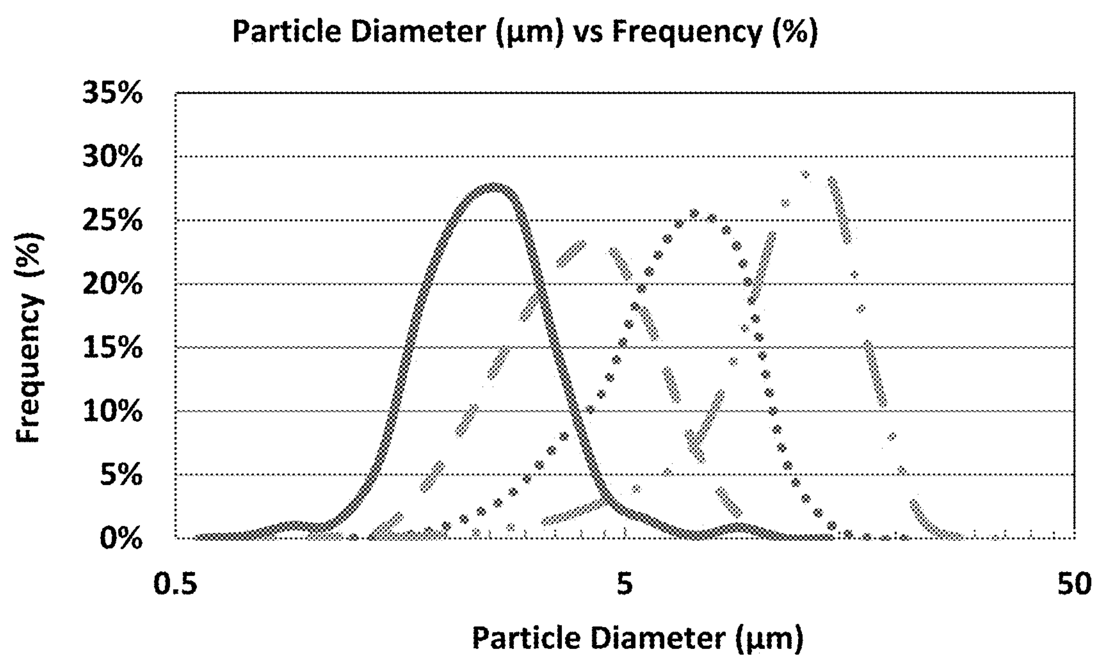
FIG. 4 is a graph showing a representative particle size distribution for an in-line process in accordance with some embodiments of the present invention.
Figure 5:
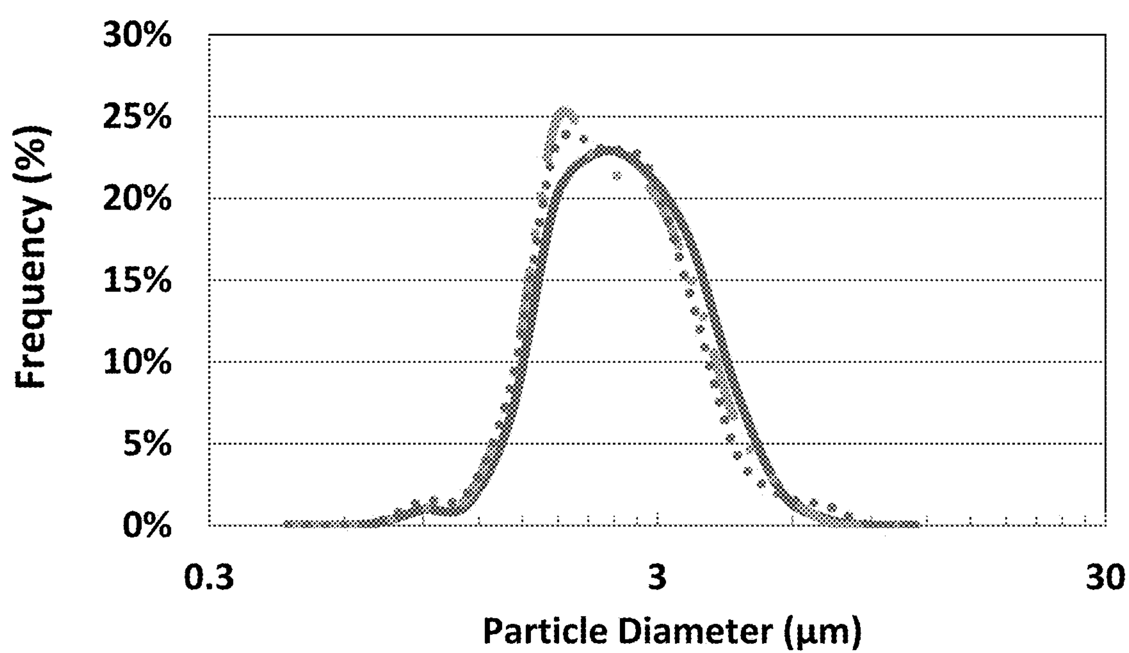
FIG. 5 is a graph showing reproducibility of particle size distribution with a small scale process.
Figure 6:
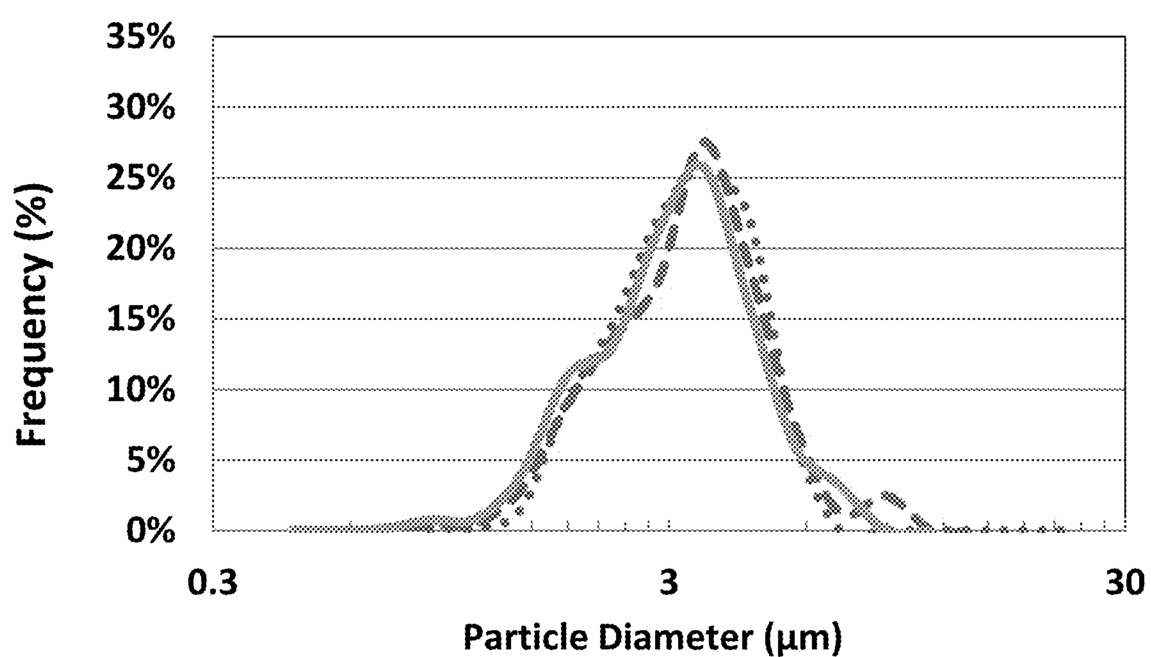
FIG. 6 is a graph showing reproducibility of particle size distribution with an in-line process in accordance with some embodiments of the present invention.

By adjusting processing parameters for a dehydration microglassification method, a variety of particle size distributions are able to be achieved (FIG. 4). In addition, a good reproducibility for the particles is achieved using both a smaller batch protocol (FIG. 5) and the inline manufacturing process described above (FIG. 6).

Figure 7:
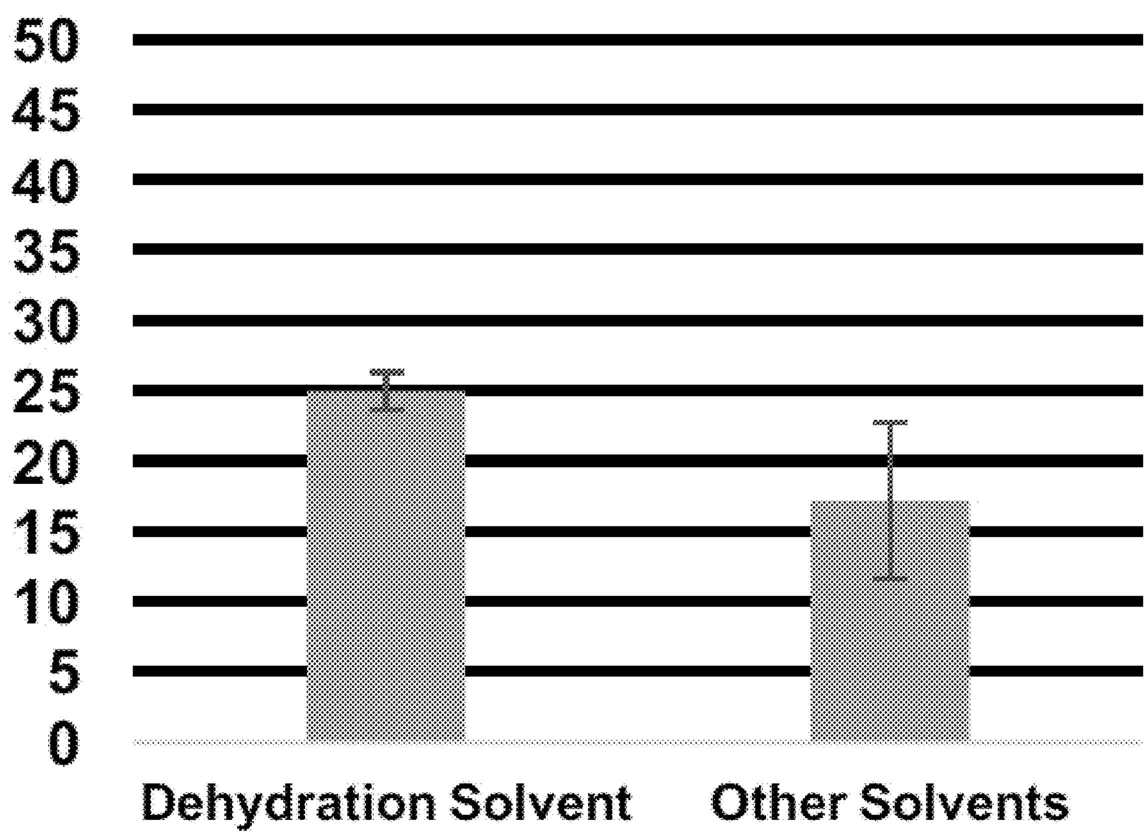
FIG. 7 is a graph showing milligrams of residual solvents remaining per gram of Microglassified™ BGG.

The amount of residual solvent present in a microglassifed product can be predictable and well below the limits (50 mg/day) permitted by the Food & Drug Administration for Class III residual solvents. FIG. 7 shows the amount of residual solvents remaining per gram of microglassified BGG.

These experiments demonstrated the feasibility of increasing material throughput using microglassification methods.

Example 3

The stability of microglassifed model proteins, including a monoclonal antibody and an enzyme, will be evaluated and the effect of processing parameters will be examined. Model proteins will be dehydrated at either the beginning (crude drug substance) or end (formulated drug substance) of downstream purification, and stability will be evaluated over 6 months under accelerated conditions. Preservation will be evaluated at the beginning and end of downstream purification, providing two potential steps for workflow to be paused.

Preservation of Extracellular Biologics

Microglassification™ will be used to preserve an antibody in culture media harvested from Chinese hamster ovary (CHO) cell lines, which are commonly used in commercial production of therapeutic proteins. Stability of the microglassifed upstream antibody and microglassifed formulated antibody will be determined at intermediate and accelerated conditions.

Upstream Processing Experiments—Crude Drug Substance Preservation:

As a model system, a non-producing CHO cell line will be grown and spiked with bovine gamma globulin (BGG) to 5 g/L. BGG will be the protein used for this task to reduce production costs, since large quantities of material are required for residual moisture and solvent analysis.

CHO cells will be cultured for 14 days in media homologous to that used in commercial production of antibody. The cells will be separated by centrifugation, and BGG or a monoclonal antibody will be added to the media to mimic antibody produced by the cells. Aliquots from the cellular media will be Microglassified™ by combining the media with emulsion solvents and/or dehydration solvents and/or washing solvents as described above. Micropipette experiments will be used to check dehydration rate, final protein concentration, and final droplet density (total solids mass per volume). The dehydration rate will be used to calculate the required residence time in the Microglassification™ process for a given particle size. Final concentration and density will set the maximum f-value (fractional water saturation) that can be used. The dehydrated and collected powder will be analyzed for size/morphology using microscopy, moisture content using Karl Fischer titration, and for residual solvent using gas chromatography (GC) according to the USP method. Any adjustments to the Microglassification™ process to account for the composition of cellular media will be made before proceeding.

The same CHO cell line will be cultured and spiked with a mAb to about 5 g/L as described above. Aliquots from the cellular media will be Microglassified™ or frozen. The dehydrated powder will be rehydrated to a concentration of 5 g/L, purified, and subsequently assayed for changes in structure using SEC and capillary electrophoresis (CE). Functionality will also be assessed via binding ELISA. As a control, the mAb will also be purified and analyzed from non-Microglassified™ cellular media. Further samples will be Microglassified™, aliquoted into crimped glass vials under nitrogen, and placed on accelerated stability for up to 6 months at 25° C. and 40° C. At predetermined time-points, samples will be rehydrated, purified, and assayed as described above. At the end of the study, the frozen samples will be thawed, purified, and analyzed as a freeze-thaw comparison.

Downstream Processing Experiments—Formulated Drug Substance Preservation:

The same mAb used for the upstream processing experiments will be used to check Microglassification™ protocols for different excipient-protein ratios (e.g., sucrose:protein at 0:1 to 1:1 weight ratios) via a design of experiments (DOE) approach. Micropipette experiments will be used to check dehydration rate, final protein concentration, and final droplet density (total solids mass per volume). The purified and formulated mAb solution will be Microglassified by combining it with emulsion solvents and/or dehydration solvents and/or washing solvents. The collected Microglassified™ powder samples will be assayed for morphology and residual moisture. Rehydrated samples will be analyzed as described above. Those compositions that maintained molecular structure will be placed on accelerated stability as described above. Controls will include frozen solutions stored at −20° C.

Preservation of Intracellular Biologics

The stability of upstream single chain antibody fragment (scFv) when Microglassified™ from fermentation broth will be compared to the stability of formulated scFv when Microglassified™ from a purified solution.

Upstream Processing Experiments—Crude Drug Substance Preservation:

Unlike antibody production from mammalian cells, which excretes the protein extracellularly, some proteins, including fusion proteins and enzymes, can be produced intracellularly from bacterial sources, requiring a cell-lysing step (e.g., homogenization) during harvesting. Microglassification™ will be conducted from whole fermentation broth. While not wishing to be bound to any particular theory, since lipids are soluble in the organic solvents used, it is expected that some of the cellular debris will be removed during Microglassification™. If cells are not completely lysed by the Microglassification™ process, samples will be Microglassified™ after cell lysis and removal of cellular debris.

A single chain variable fragment (scFv) that binds beta-galactosidase will be produced by *E. coli*. As described above, aliquots will be Microglassified™, this time from fermentation broth containing whole cells. The fermentation broth and cells will be combined with emulsion solvents and/or dehydration solvents and/or washing solvents as described above. Micropipette experiments will be used to check dehydration rate, final protein concentration, and final droplet density (total solids mass per volume). The dehydrated powder will be analyzed for size/morphology using microscopy, moisture content using Karl Fischer titration, and for residual solvent using gas chromatography (GC) according to the USP method. Any adjustments to the Microglassification™ process to account for the composition of cellular media will be made.

Aliquots from the fermentation broth will be Microglassified™ or frozen. The dehydrated powder will be rehydrated to a concentration of 5 g/L, purified, and subsequently assayed for changes in structure using SEC and capillary electrophoresis (CE). Functionality will also be assessed via ELISA. As a control, the scFv will also be purified and analyzed without Microglassification™. Further samples will be Microglassified™, aliquoted into crimped glass vials under nitrogen, and placed on accelerated stability for up to 6 months at 25° C. and 40° C. At pre-determined time-points, samples will be rehydrated, purified, and assayed as described above. At the end of the study, the frozen samples will be thawed, purified, and analyzed as a freeze-thaw comparison.

Downstream Processing Experiments—Formulated Drug Substance Preservation:

The same scFv as used in the upstream processing experiments will be used to check Microglassification™ protocols for different excipient-protein ratios (e.g., sucrose:protein at 0:1 to 1:1 weight ratios) via a design of experiments (DOE) approach. Purified scFv will be used. Micropipette experiments will be used to check dehydration rate, final protein concentration, and final droplet density (total solids mass per volume). The purified and formulated scFv solution will be Microglassified by combining it with emulsion solvents and/or dehydration solvents and/or washing solvents. The collected Microglassified™ powder samples will be assayed for morphology and residual moisture. Rehydrated samples will be analyzed as described above. Those compositions that maintained molecular structure will be placed on accelerated stability as described above. Controls will include frozen solutions stored at −20° C.

Example 4

A pre-emulsion step will be utilized in a dehydration method to dehydrate water soluble components present in a liquid cell culture medium. In the pre-emulsion step, an emulsification solvent will be used that does not significantly dissolve water, so it does not dehydrate the liquid cell culture medium comprising a water soluble component and/or biologic. The liquid cell culture medium and emulsification solvent will be mixed (e.g., by vortexing, stirring, homogenizing, extruding, and/or by adding or spraying the aqueous phase into the solvent phase), thereby forming a coarse emulsion. This coarse emulsion will then be combined with a volume of a dehydration solvent (which could be the same or different from the emulsification solvent) sufficient to dissolve the water.

A hand extruder including two glass Hamilton syringes that are connected such that the contents of one pass through the extrusion chamber and into the other syringe may be used. Alternatively, for inline production, a static mixer or homogenizer could be used instead of a hand extruder for batch production.

Example 5

Figure 8:
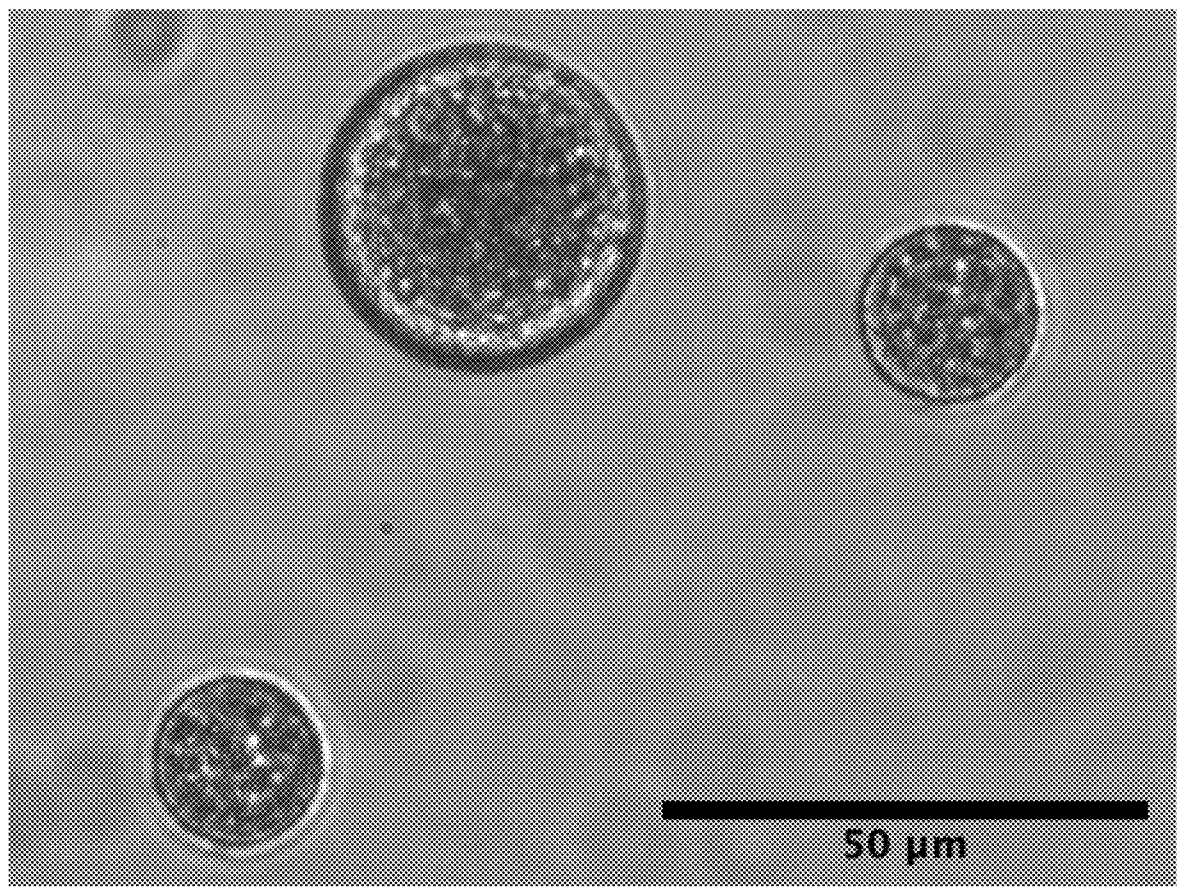
FIG. 8 is an image of a suspension of microglassified particles in pentanol following contact of a cell composition and pentanol according to some embodiments of the present invention.

*Micrococcus lysodeikticus* (ML) cells (lyophilized) were suspended at 50 mg/mL (dry weight) in 150 mM phosphate buffer to provide a cell composition. 49 μL of the cell composition was quickly added dropwise to 1 mL pentanol and the mixture vortexed for 30 seconds. FIG. 8 shows dehydrated particles from the cell composition that are suspended in the pentanol dehydration solvent.

Example 6

Figure 9:
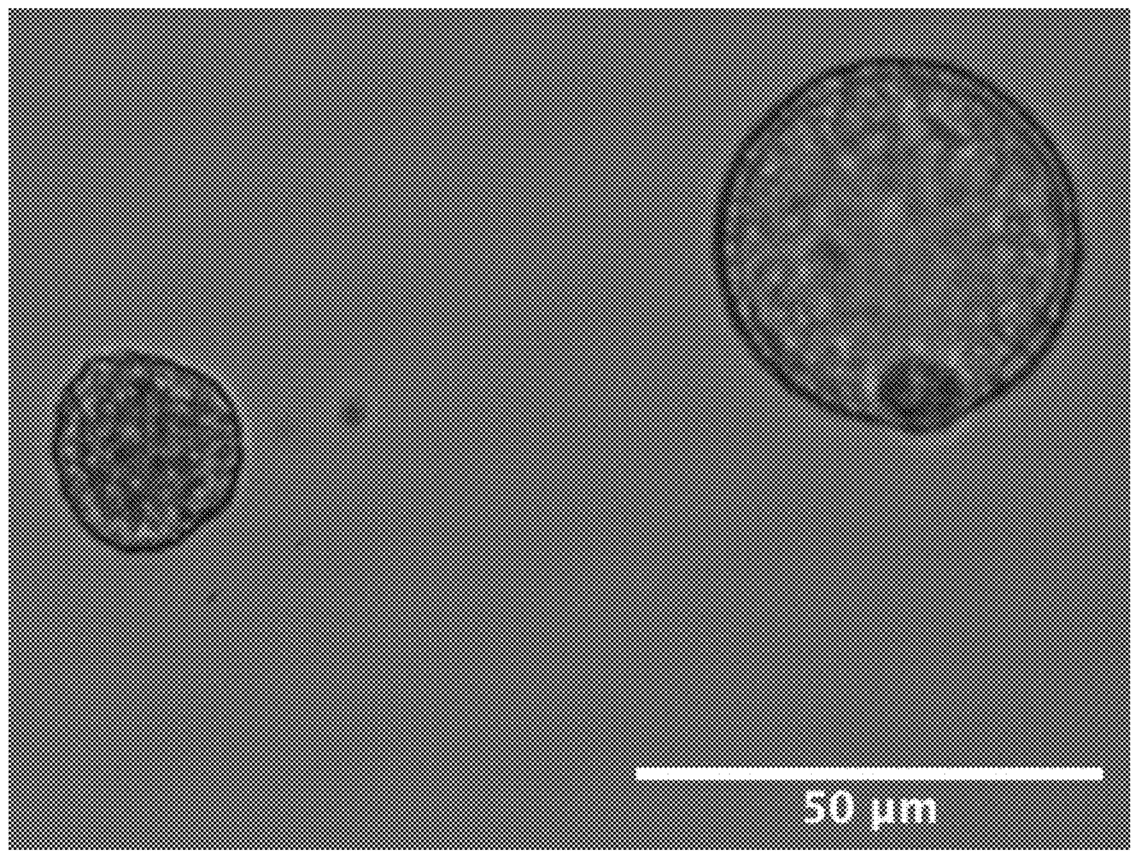
FIG. 9 is an image of a suspension of microglassified particles in butyl lactate following contact of a cell composition and butyl lactate according to some embodiments of the present invention.

ML cells were suspended at 14.2 mg/mL (dry weight) in water. 31 μL of the cell composition was quickly added to 700 μL of butyl lactate and the mixture vortexed for 30 seconds. FIG. 9 shows dehydrated particles from the cell composition that are suspended in the butyl lactate dehydration solvent. The suspension of dehydrated particles was centrifuged, the dehydration solvent removed by pipette, and residual solvent removed under overnight vacuum. The resulting powder was reconstituted by adding 800 μL water. As one of skill in the art will recognize, whole cell suspensions have a turbidity that is greater than a lysed suspension of the cells. Turbidity of the reconstituted cells was measured at 450 nm and compared to dilutions of the unprocessed cell suspension. The cells dehydrated in butyl lactate had 76±7% (n=3) lower turbidity than the starting cell suspension (diluted to the same concentration), demonstrating that the cells dehydrated in butyl lactate were lysed during the dehydration process.

Example 7

Figure 10:
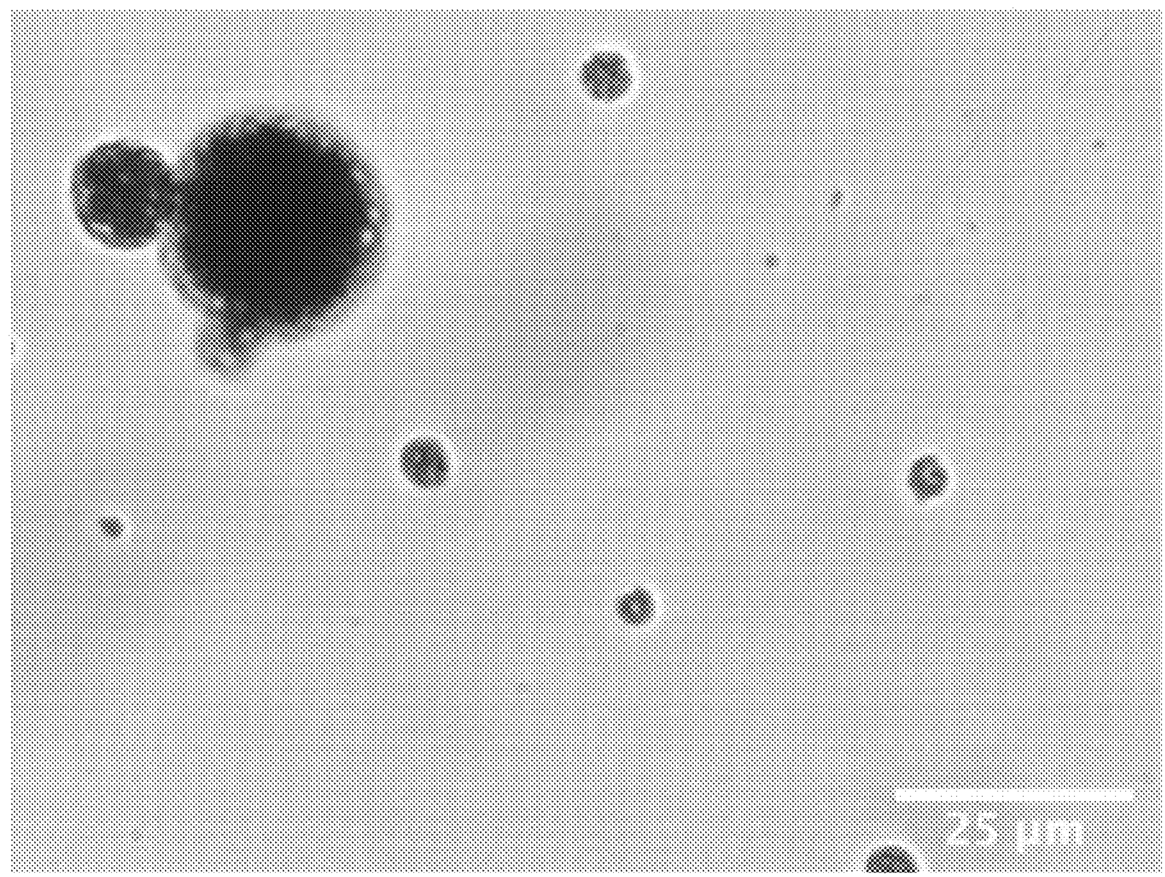
FIG. 10 is an image of a suspension of microglassified particles in pentanol following contact by vortexing of a cell composition and pentanol according to some embodiments of the present invention.
Figure 11:
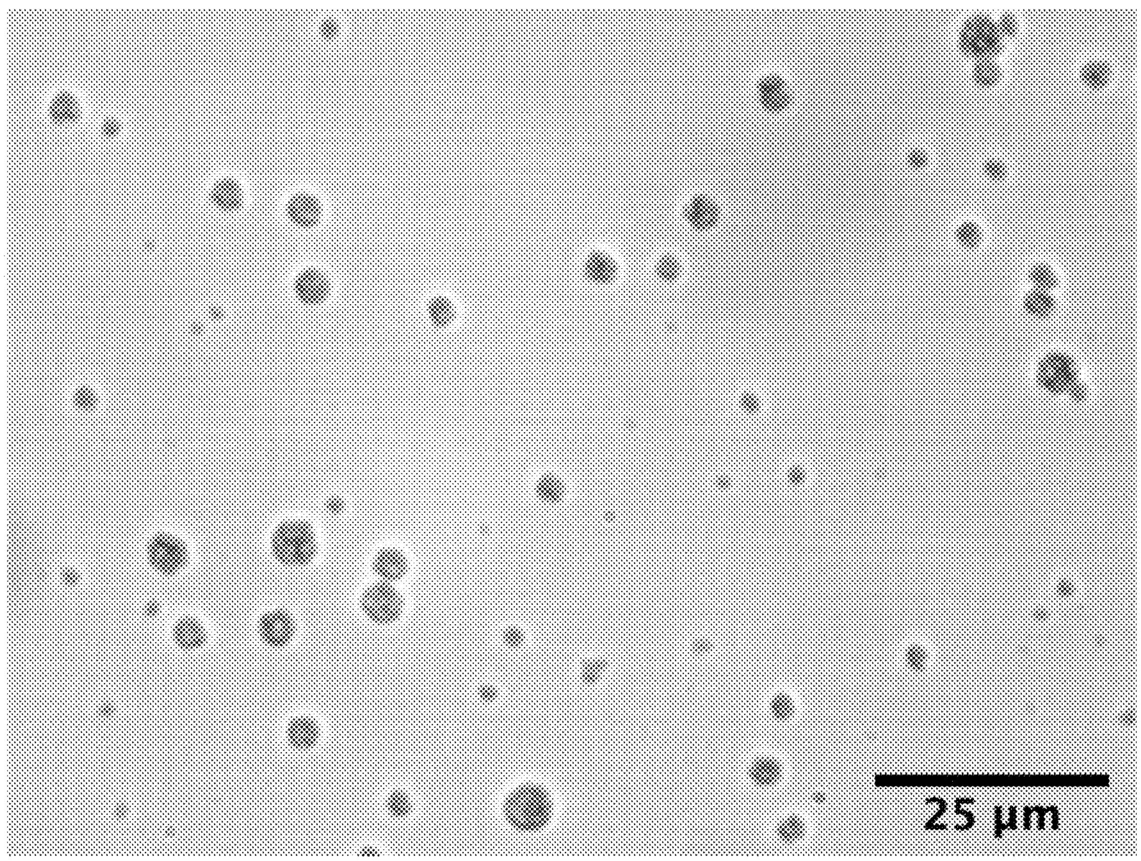
FIG. 11 is an image of a suspension of microglassified particles in pentanol following contact by homogenization of a cell composition and pentanol according to some embodiments of the present invention.

ML cells were suspended in water at 14.2 mg/mL (dry weight). 70 μL of the cell composition was quickly added to 2.5 mL of pentanol and the mixture vortexed or homogenized for 30 seconds. FIG. 10 shows dehydrated particles from the vortexed cell composition and FIG. 11 shows dehydrated particles from the homogenized cell composition, both suspended in the pentanol dehydration solvent. As can be seen in FIG. 11, using a homogenizer provided smaller particles, but with a similar morphology to those that were vortexed.

The suspension of dehydrated particles was centrifuged, the dehydration solvent removed by pipette, and residual solvent removed under overnight vacuum. The resulting powder was reconstituted by adding 1.9 mL water. The cells vortexed and dehydrated in pentanol had 50±6% (n=3) lower turbidity than the starting cell suspension (diluted to the same concentration).

Figure 12:
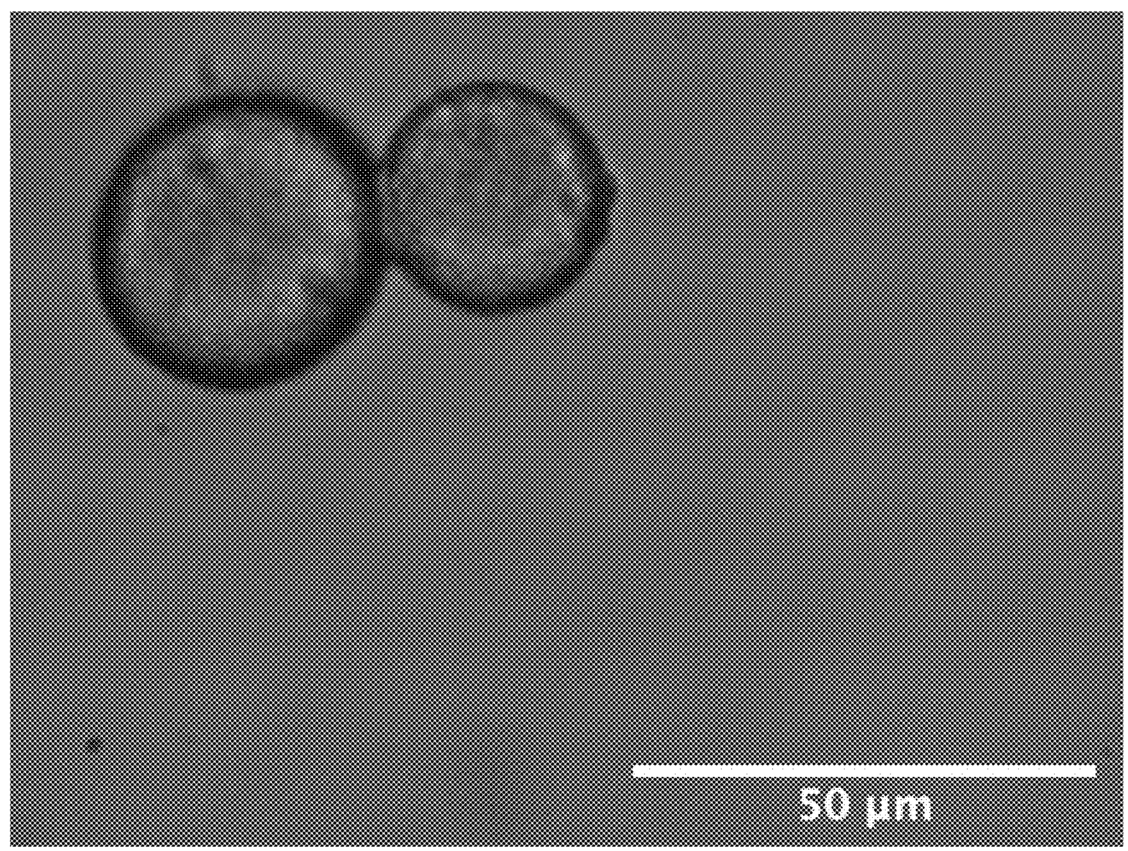
FIG. 12 is an image of a suspension of microglassified particles in pentanol following contact by vortexing of a highly concentrated cell composition and pentanol according to some embodiments of the present invention.

ML cells were suspended in water at 195 mg/mL (dry weight) to approximate a concentrated slurry. 170 μL of the cell composition was quickly added to 2.5 mL of pentanol and the mixture vortexed for 30 seconds. FIG. 12 shows dehydrated particles from the cell composition that are suspended in the pentanol dehydration solvent. These particles have a similar morphology to those in FIG. 11, but are larger due to the higher starting concentration.

Example 8

An impure dehydration solvent obtained from a microglassification method will be brought into contact with a hygroscopic material. The hygroscopic material may be any material (e.g., a solid, liquid, or gas material) that is insoluble in the solvent in question. Exemplary materials include, but are not limited to, magnesium sulphate, sodium sulphate, 3A molecular sieves, super absorbent polymers, silica, alumina, bubble column with dry air, etc. Once the material has spent sufficient time with the impure dehydration solvent, and consequently removed by methods described above, it will be a purified or semi-purified solvent.

Example 9

An impure dehydration solvent obtained from a microglassification method will go through a distillation process to yield a purified or semi-purified solvent.

Example 10

An impure dehydration solvent obtained from a microglassification method will be chilled or heated in order to reduce the solubility of impurities in the material or freeze other materials. Once some materials have crystallized or precipitated, they can be removed by methods described above, to yield a purified or semi-purified solvent.

Example 11

Figure 13:
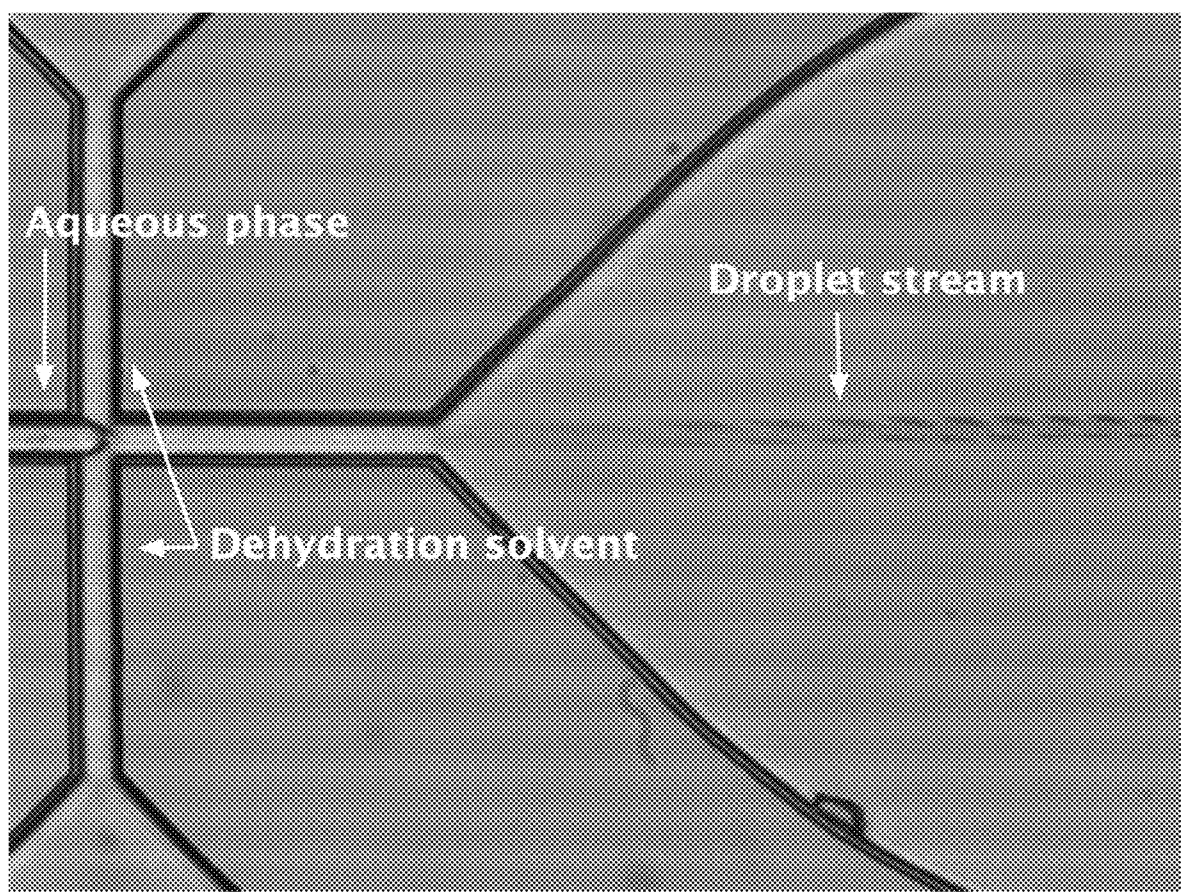
FIG. 13 is an image of a microfluidic device being used in microglassification according to embodiments of the present invention.
Figure 14:
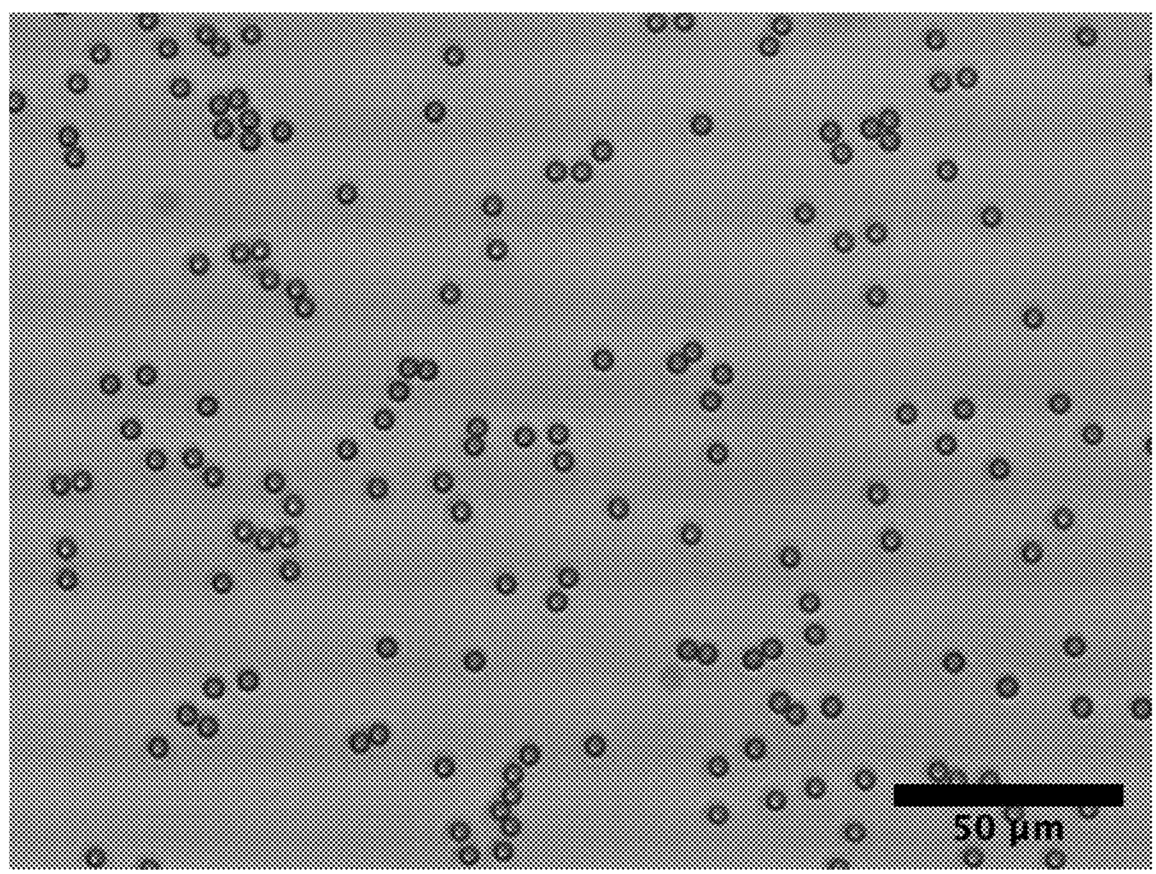
FIG. 14 is an image of particles produced using the microfluidic device shown in FIG. 10. The average particle diameter in 4.8 μm.

A protein solution was microglassified using a microfluidics device containing a crossflow junction (14×17 μm) as shown in FIG. 13. The device was constructed of quartz with a hydrophobic coating to allow formation of a water-in-oil emulsion. The aqueous phase (45 mg/mL lysozyme) and dehydration medium (1-pentanol) were delivered via pressure pumps at flow rate ratios ranging from 1:44 to 1:258 (water:dehydration solvent). The aqueous phase was fed through the center channel, forming droplets pinched off by the dehydration medium entering from the side channels. FIG. 14 shows collected particles having an average diameter of 4.8 μm that were produced using a flow rate ratio of 1:46. Depending on the dehydration solvent used and the droplet size initially formed, the droplets may be dehydrated and solidified before leaving the chip or may be collected in an external vessel. This method allows for the production of very uniform particles.

Example 12

Figure 15:
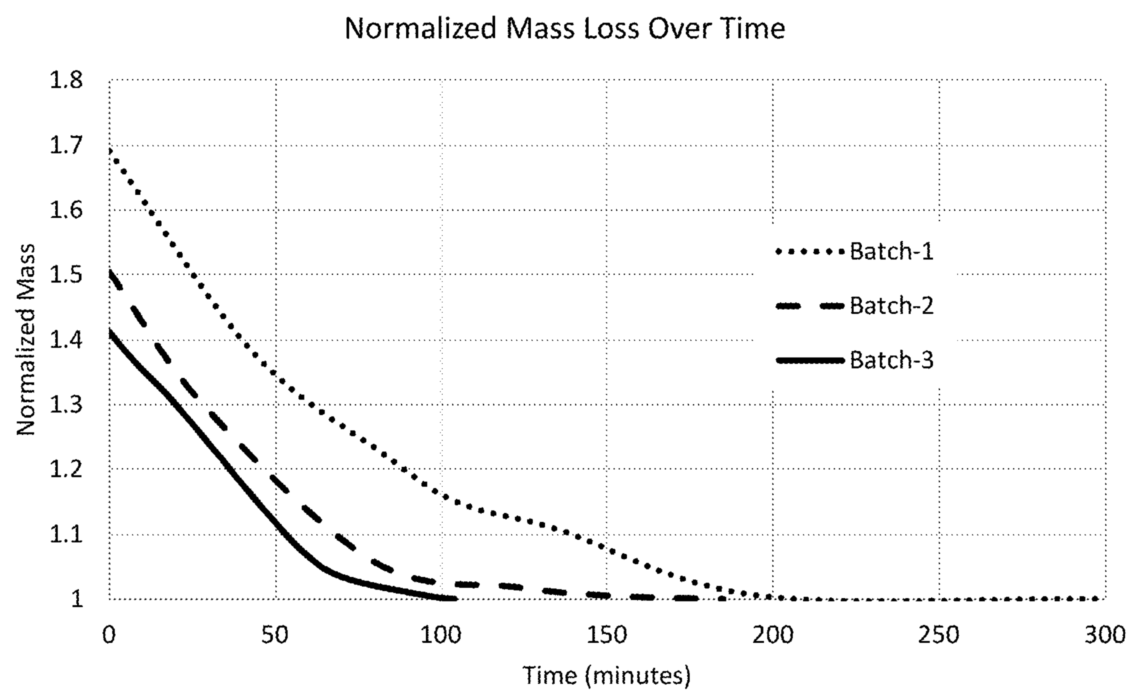
FIG. 15 is a graph of mass loss over time during nitrogen drying of a protein powder.

Collected particles may be further dried by one of several methods to remove residual solvent, resulting in a dry powder. FIG. 15 shows mass loss over time during drying by exposure to dry nitrogen. The mass shown in FIG. 15 has been normalized to the final mass of dry powder, which consisted of 75% bovine serum albumin and 25% other solid components. The majority of mass lost is residual dehydration and wash solvent, which was octanol and pentanol for the particles in FIG. 15. Batch-1 was 617 mg of powder dried at flow rates between 1 and 1.5 L/min. The amount of solvent and moisture removed was 427 mg. Batch-2 was 831 mg of powder dried at a flow rate of 2 L/min. The amount of solvent and moisture removed was 419 mg. Batch-3 was 890 mg of powder dried at flow rates between 1 and 1.8 L/min. The amount of solvent and moisture removed was 367 mg.

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A composition comprising:

a plurality of particles, wherein each particle of the plurality of particles comprises an amorphous protein and the amorphous protein is present in each particle in an amount of at least 65% by weight of the particle, wherein each particle of the plurality of particles is a solid particle that has a water content of less than 10% and a water activity of 0.25 or less, and wherein the composition comprises aggregates of the protein in an amount less than 5% by weight of the protein in the composition.

2. The composition of claim 1, wherein the protein is an antibody or a fragment thereof.

3. The composition of claim 1, wherein the composition comprises aggregates of the protein in an amount less than 3% by weight of the protein in the composition.

4. The composition of claim 1, further comprising a sugar.

5. The composition of claim 1, further comprising a surfactant.

6. The composition of claim 1, further comprising an antioxidant.

7. The composition of claim 1, wherein the plurality of particles, upon contact with an aqueous solution, dissolve in the aqueous solution.

8. The composition of claim 1, wherein the plurality of particles are suspended in the composition.

9. The composition of claim 8, wherein the plurality of particles are suspended in an ester.

10. The composition of claim 8, wherein the plurality of particles are suspended in a C1-C20 ester containing compound.

11. The composition of claim 1, wherein the plurality of particles have a size of 2 μm to 20 μm.

12. The composition of claim 1, wherein the protein in the plurality of particles has an activity, upon dissolution in a solution, that is within ±30% of the activity of the protein prior to the formation of the plurality of particles.

13. The composition of claim 1, wherein the composition comprises at least 25% of the solid particles by weight of the composition.

14. The composition of claim 1, wherein the composition comprises at least 50% of the solid particles by weight of the composition.

15. The composition of claim 1, wherein the composition comprises at least 60% of the solid particles by weight of the composition.

16. The composition of claim 1, wherein the composition, after storage at a temperature of about 4° C. to about 10° C. for at least 2 years, comprises aggregates of the protein in an amount less than 10% by weight of the protein.

17. The composition of claim 1, wherein the protein, after storage of the composition at a temperature of about 4° C. to about 10° C. for at least 2 years, has an activity, upon dissolution in a solution, that is within ±30% of the activity of the protein prior to the formation of the plurality of particles.

18. The composition of claim 1, wherein the composition, after storage at a temperature of about 25° C. for at least 1 year, comprises aggregates of the protein in an amount less than 10% by weight of the protein.

19. The composition of claim 1, wherein the composition, after storage at a temperature of about 40° C. for at least 3 months, comprises aggregates of the protein in an amount less than 10% by weight of the protein.

20. The composition of claim 1, wherein the plurality of particles are microspheres, wherein the protein of the microsphere retains at least 90% of its biological activity, and wherein the protein of the microsphere maintains a folded structure.

21. A composition comprising:

a solvent and a plurality of particles, wherein each particle of the plurality of particles is a solid particle that comprises an amorphous protein and each particle of the plurality of particles has a water content of less than 10% and a water activity of less than 0.75, wherein the composition comprises at least 25% of the solid particles by weight of the composition, and wherein the composition comprises aggregates of the protein in an amount less than 5% by weight of the protein in the composition, and wherein the solid particles of the plurality of particles are suspended in the solvent.

22. The composition of claim 21, wherein the protein is an antibody or a fragment thereof.

23. The composition of claim 21, further comprising a surfactant.

24. The composition of claim 21, further comprising an antioxidant.

25. The composition of claim 21, wherein the plurality of particles are microspheres.

26. The composition of claim 21, wherein the solvent is an ester.

27. The composition of claim 21, wherein the solvent is a C1-C20 ester containing compound.

28. The composition of claim 21, wherein the protein in the plurality of particles has an activity, upon dissolution in a solution, that is within ±30% of the activity of the protein prior to the formation of the plurality of particles.

29. The composition of claim 21, wherein the composition, after storage at a temperature of about 40° C. for at least 3 months, comprises aggregates of the protein in an amount less than 10% by weight of the protein.

30. The composition of claim 21, wherein the composition comprises 40% to 60% of the solid particles by weight of the composition, wherein the amorphous protein is present in each particle of the plurality of particles in an amount of at least 65% by weight of the particle, and wherein the water activity of each particle of the plurality of particles is 0.25 or less.

* * * * *

UNITED STATES PATENT AND TRADEMARK OFFICE

CERTIFICATE OF CORRECTION

PATENT NO. : 11,795,429 B2
APPLICATION NO. : 18/058306
DATED : October 24, 2023
INVENTOR(S) : Bitterfield et al.

It is certified that error appears in the above-identified patent and that said Letters Patent is hereby corrected as shown below:

In the Claims

Column 28, Lines 23-25, Claim 21: Please remove the following text: "wherein the composition comprises aggregates of the protein in an amount less than 5% by weight of the protein in the composition, and"

Signed and Sealed this
Twenty-sixth Day of March, 2024

Katherine Kelly Vidal

Katherine Kelly Vidal
*Director of the United States Patent and Trademark Office*